(12) United States Patent
Jacob et al.

(10) Patent No.: US 11,730,697 B2
(45) Date of Patent: Aug. 22, 2023

(54) OCULAR DRUG DELIVERY DEVICES

(71) Applicants: Bausch Health Americas, Inc., Bridgewater, NJ (US); Louisiana State University Agricultural and Mechanical College, Baton Rouge, LA (US)

(72) Inventors: Jean Theresa Jacob, New Orleans, LA (US); Kevin John Halloran, Somerset, NJ (US); Yuri McKee, Atlanta, GA (US)

(73) Assignees: Bausch Health Americas, Inc., Bridgewater, NJ (US); Louisiana State University Agricultural and Mechanical College, Baton Rouge, LA (US)

(*) Notice: Subject to any disclaimer, the term of this patent is extended or adjusted under 35 U.S.C. 154(b) by 1066 days.

(21) Appl. No.: 16/241,558

(22) Filed: Jan. 7, 2019

(65) Prior Publication Data
US 2019/0133934 A1    May 9, 2019

Related U.S. Application Data

(60) Division of application No. 14/087,864, filed on Nov. 22, 2013, now abandoned, which is a continuation of application No. 12/916,398, filed on Oct. 29, 2010, now abandoned.

(60) Provisional application No. 61/391,040, filed on Oct. 7, 2010, provisional application No. 61/256,915, filed on Oct. 30, 2009.

(51) Int. Cl.
| | | |
|---|---|---|
| *A61K 9/00* | (2006.01) | |
| *A61K 31/00* | (2006.01) | |
| *A61K 47/36* | (2006.01) | |
| *C08L 1/28* | (2006.01) | |
| *A61K 31/133* | (2006.01) | |
| *A61K 31/216* | (2006.01) | |
| *A61K 31/7036* | (2006.01) | |
| *A61K 38/12* | (2006.01) | |
| *A61K 38/13* | (2006.01) | |

(52) U.S. Cl.
CPC ............ *A61K 9/0051* (2013.01); *A61K 31/00* (2013.01); *A61K 31/133* (2013.01); *A61K 31/216* (2013.01); *A61K 31/7036* (2013.01); *A61K 38/12* (2013.01); *A61K 38/13* (2013.01); *A61K 47/36* (2013.01); *C08L 1/284* (2013.01)

(58) Field of Classification Search
None
See application file for complete search history.

(56) References Cited

U.S. PATENT DOCUMENTS

| | | | |
|---|---|---|---|
| 5,516,530 A * | 5/1996 | Lo | A61K 9/2095 424/473 |
| 8,409,606 B2 * | 4/2013 | Sawhney | A61B 17/12099 424/427 |

* cited by examiner

*Primary Examiner* — Michael G. Hartley
*Assistant Examiner* — Lance W Rider
(74) *Attorney, Agent, or Firm* — Andrew J. Anderson, Esq.; Harter Secrest & Emery LLP

(57) ABSTRACT

A method of forming an ocular delivery device includes exposing a solid, shaped cellulose polymer to a solution including an active pharmaceutical ingredient (API) and a solvent capable of solubilizing the API, wherein the polymer absorbs at least a portion of the solution, including the API and solvent. The method may further include removing at least a portion of the absorbed solvent from the polymer by allowing the absorbed solvent to evaporate from the polymer or by drying the polymer. A variety of cellulose polymers may be used, including hydroxypropyl cellulose. A variety of APIs may be used, including Cyclosporine, Tobramycin and Vancomycin. Ocular delivery devices prepared by the methods may be used to treat a variety of eye disorders.

20 Claims, 22 Drawing Sheets

OCULAR DRUG DELIVERY DEVICES

This application claims priority from U.S. Provisional Application 61/256,915, filed 30 Oct. 2009, and U.S. Provisional Application 61/391,040, filed 7 Oct. 2010, incorporated herein by reference in their entirety.

BACKGROUND

Ocular inserts are used to treat a variety of disorders of the eye. For example, commercially available Lacrisert®, is used to treat dry eye. Lacrisert® is a sterile, translucent, rod-shaped, water soluble, ophthalmic insert made of hydroxypropyl cellulose for administration into the inferior cul-de-sac of the eye by the patient or medical practitioner. Once inserted, the hydroxypropyl cellulose slowly dissolves in the eye over a period of several hours to a day. In the case of dry eye treatment, hydroxypropyl cellulose aids in tear retention and increases tear viscosity, to relieve the symptoms associated with dry eye.

Polymeric ocular inserts, including Lacrisert®, are typically prepared by polymeric molding processes such as compression molding, injection molding, or extrusion. In each of these processes, the polymers (and any ingredients to be incorporated into the insert), are exposed to elevated temperatures (e.g., temperatures from about 80° C. to about 400° C.). However, many useful active pharmaceutical ingredients (API) are thermally unstable at these temperatures. Thus, the types of APIs that can be incorporated into many polymeric ocular inserts are limited to those that can survive the high temperature polymeric molding processes. Moreover, these conventional molding processes, which require specially designed equipment, are time consuming, complicated, and expensive. Another method of forming polymeric ocular inserts involves film casting, in which the polymer and any associated ingredients (e.g., an API) to be incorporated into the insert are often dissolved at elevated temperatures. Not only does this method often require elevated temperatures, but also, solvents capable of dissolving both the polymer and an API are required. In general the methods described above do not allow the conditions for forming molded polymer to be optimized independently of the conditions for loading the polymer with other ingredients, such as an API.

Although some eye disorders may be treated with ocular inserts, certain eye disorders are typically treated with eye drops. For example, fortified Tobramycin and Vancomycin eye drops are often used to treat bacterial infections of the corneal stroma. Bacterial keratitis is one such type of infection. Bacterial keratitis is seen in approximately 3.02 of every 1000 clinic visits, although the incidence rate is increased within the contact lens wearing population. Of all bacterial keratitis cultures, 28.9% are attributed to *Staphlococcus aureus* (*S. aureus*). Severe bacterial infections of the cornea stroma require immediate and intense treatment to prevent the loss of vision, the cornea, and even the entire eye. Often inpatient hospitalization with intensive nursing care is required to administer the drugs via eye drops every half hour. Such care is time consuming, expensive, and invasive to the patient. In addition, approximately 90-95% of topical drops are cleared very quickly from the tear film by draining into the nose or spilling onto the cheek. Achieving a significant concentration of drug on the surface of the eye and within the cornea presents a daunting challenge. With current topical treatment modalities the prognosis for severe infections of the cornea remains very poor.

SUMMARY

Provided herein are ocular delivery devices, methods of forming the ocular delivery devices, and methods of using the ocular delivery devices to treat a variety of eye disorders. The methods involve exposing a solid, shaped cellulose polymer to a solution including an API and a solvent capable of solubilizing the API. During this step, the polymer absorbs at least a portion of the solution, including the API and solvent, thereby becoming loaded with the API. The methods further involve removing at least a portion of the absorbed solvent from the polymer by allowing the absorbed solvent to evaporate from the polymer or by drying the polymer, optionally under vacuum. Thus, the methods provide loaded polymeric ocular inserts without requiring any excessive temperatures. Not only are the disclosed methods faster, simpler, and less expensive than conventional methods, but also, the disclosed methods can allow the conditions for the polymeric molding process to be optimized independently from the conditions for loading the polymer with API. As a result, the disclosed ocular delivery devices may be formed with a broader range of APIs than is possible with conventional methods for forming ocular inserts. Finally, the disclosed ocular delivery devices are capable of providing more effective, more convenient treatments for a variety of eye disorders, including bacterial keratitis.

By "shaped" is meant that the cellulose polymer is three dimensional, having a length, width (e.g., diameter) and height. In preferred embodiments of the invention the cellulose polymer has a length falling in the range of about 0.5 mm to about 7 mm, preferably about 1 to about 5 mm, and more preferably from about 2 to about 4 mm. Likewise, an embodiment of the cellulose polymer has a width (or diameter in the case of cylinders or discs) falling in the range of about 0.5 mm to about 4 mm, preferably about 1 to about 3 mm, and more preferably from about 1 to about 2 mm. Where the embodiment of the cellulose polymer has a height dimension, then the height falls in the range of about 0.5 to about 3 mm, preferably about 1 to about 2.5 mm, and more preferably from about 1 to about 2 mm. Hence the cellulose polymer of the invention may have a shape that can be described as rod-like, disc-like, block-shaped, elongated, football-shaped, rectangular-shaped, half-cylinder-shaped or semi-cylinder shaped and the like. The cellulose polymer may have smooth surfaces (as in a cylinder or cube) or irregular surfaces like those of a raisin (i.e., non-smooth, cylindrical surfaces or raisin-like). The cellulose polymer may also be swollen and/or irregularly shaped. Still in other embodiments, a cellulose polymer has dimensions that are not the same as those exhibited by commercially available Lacrisert®, which is shaped like a smooth cylinder whose dimensions are 1.27 mm in diameter and 3.5 mm in length. Moreover, whereas the optical characteristics of the surface of commercially available Lacrisert®, is visually opaque, the surface of a cellulose polymer of the present invention can be described as translucent. However, depending on the nature of the drug being loaded into the Lacrisert®, the surface of the cellulose polymer of the present invention can appear to be similar to, more translucent than, or more opaque than that of commercially available Lacrisert®.

The solid, shaped cellulose polymers may be prepared by methods known in the art. According to some embodiments, the solid, shaped polymers are prepared via extrusion, molding, or machining. For example, the polymers may be extruded with an extrusion apparatus such as a single- or twin-screw extruder. In some embodiments, the polymers are molded using compression molding or solution molding. In some embodiments, the solid, shaped cellulose polymers are prepared from powders of the cellulose polymer, including without limitation, by hot melt extrusion of the cellulose polymer. Thus, in such embodiments, the solid, shaped cellulose polymers are not powders.

In one aspect, a method of forming an ocular delivery device is provided, including placing a solid, shaped cellulose polymer in a vessel adapted to restrict the swelling of the polymer in at least one direction (e.g., axially, radially and the like); exposing the polymer, while in the vessel, to a solution comprising an active pharmaceutical ingredient and a solvent capable of solubilizing said active pharmaceutical ingredient, where the polymer absorbs at least a portion of the solution, including the active pharmaceutical ingredient and solvent, allowing the absorbed solvent to evaporate from the polymer or drying the polymer; and freeing the polymer from the vessel, to thereby form the ocular delivery device. In some embodiments, the at least one direction is a radial direction. In others the at least one direction might be lengthwise or longitudinal. In some embodiments, the shape and dimension of an interior surface of the vessel substantially matches the shape and dimension of an exterior surface of the polymer. In some embodiments, the vessel is a tubular vessel. In some embodiments, the vessel is a trough-like vessel. In some embodiments, the interior surface of the vessel is coated with a surface-release agent. Suitable surface-release agents include, but are not limited to, dimethyldichlorosilane, polysiloxane, octamethylcyclotetrasiloxane, (dimethylamino)trimethylsilane, N-(trimethylsilyl)dimethylamine, hexamethyldisilazane/trimethylchlorosilane/1-chloronaphthalene, chlorotributylsilane, tributylsilylchloride and the like. In some embodiments, the ocular delivery device is capable of releasing the active pharmaceutical ingredient upon exposure of the ocular delivery device to a medium. In some embodiments, the medium includes tear fluid. In some embodiments, substantially all of the absorbed solvent is allowed to evaporate from the polymer or wherein the polymer is dried to remove substantially all of the absorbed solvent from the polymer. In some embodiments, the polymer is hydroxypropyl cellulose. In some embodiments, the active pharmaceutical ingredient is thermally unstable above about 80° C.

In some embodiments, the ocular delivery device is capable of releasing the active pharmaceutical ingredient for extended periods of time from 1 hour up to 24 hours. In some embodiments, the release of the active pharmaceutical ingredient from the ocular delivery device is substantially zero-order from about two to about six hours after exposing the ocular delivery device to the medium.

In another aspect of the invention a method is provided for releasing an active pharmaceutical ingredient from the ocular delivery device, wherein the ocular delivery device includes a half-cylinder (or semi-cylinder) of a cellulose polymer and an active pharmaceutical ingredient, the method including contacting the ocular delivery device with an aqueous solution or medium, including animal tears. Suitable cellulose polymers are those as described above. In some embodiments, the half-cylinder is a Lacrisert® ocular insert that has been cut lengthwise, either in equal or unequal portions. In some embodiments, at least about 5%, at least about 10%, at least about 15%, at least about 20%, at least about 25%, at least about 35%, at least about 45%, at least about 60%, about 5% to about 60%, or about 5% to about 45% of the active pharmaceutical ingredient is released over a time period of an hour. In some embodiments, at least about 20%, at least about 25%, at least about 30%, at least about 35%, at least about 40%, at least about 45%, at least about 50%, at least about 60%, at least about 70%, at least about 80%, about 20% to about 80%, or about 20% to about 65% of the active pharmaceutical ingredient is released over about 2 hours. In some embodiments, at least about 20%, at least about 25%, at least about 30%, at least about 35%, at least about 40%, at least about 45%, at least about 50%, at least about 60%, at least about 70%, at least about 80%, about 20% to about 80%, or about 20% to about 65% of the active pharmaceutical ingredient is released over about 4 hours. See also FIGS. 13, 14, 16, and 20, hereinbelow.

In some embodiments, about 50% of the active pharmaceutical ingredient is released in about 5 hours. In some embodiments, at least about 90% of the active pharmaceutical ingredient is released in about 5 hours.

In some embodiments, the identification of API release from the ocular drug delivery device is performed in vitro or in vivo. When performed in vitro such methods may be used for identifying active pharmaceuticals agents that can be, or need to be, delivered to the eye at a certain rate. When performed in vivo, such methods may be used as animal models of ocular drug delivery. When released in vivo in humans, the method may lead to an alleviation of one or more negative effects associated with a medical condition, especially an ophthalmic condition when released in or on a human eye.

In another aspect, a method of forming an ocular delivery device includes exposing a solid, shaped cellulose polymer to a solution comprising an active pharmaceutical ingredient and a solvent capable of solubilizing said active pharmaceutical ingredient, where the polymer absorbs at least a portion of the solution, including the active pharmaceutical ingredient and solvent; and removing substantially all of the absorbed solvent from the polymer by, for example, allowing substantially all of the absorbed solvent to evaporate from the polymer or drying the polymer optionally under vacuum, thereby forming the ocular delivery device.

In another aspect, a method of forming an ocular delivery device including exposing a solid, shaped hydroxypropyl cellulose polymer to a solution comprising an active pharmaceutical ingredient and a solvent capable of solubilizing said active pharmaceutical ingredient, where the polymer absorbs at least a portion of the solution, including the active pharmaceutical ingredient and solvent; and allowing the absorbed solvent to evaporate from the polymer or drying the polymer, thereby forming the ocular delivery device.

In another aspect, an ocular delivery device is provided as prepared according to any of the described methods.

In another aspect a method of forming an ocular delivery device in provided, which method includes placing a half-cylinder of a solid cellulose polymer in a trough, and exposing the half-cylinder to a solution including an active pharmaceutical ingredient and a solvent capable of solubilizing the active pharmaceutical ingredient. In some embodiments of the method, the half-cylinder absorbs at least a portion of the solution, including the active pharmaceutical ingredient and the solvent, thereby forming the ocular delivery device. In some embodiments, the trough is adapted to restrict swelling of the half-cylinder in at least one direction. In some embodiments, the method further includes allowing the absorbed solvent to evaporate from the half-cylinder or drying the half-cylinder after exposure to the solution of active pharmaceutical ingredient. In some embodiments, the method further includes freeing the ocular delivery device from the trough. In preferred embodiments, the active pharmaceutical ingredient is Acebutolol, Acyclovir, Betaxolol, Bimatoprost, Brimonidine Tartrate, Brinzolamide, Bromfenac Sodium, Cefazolin, Cephalexin, Cephadroxil, Ciprofloxacin, Ciprofloxacin HCl, Cyclosporine, Dexamethasone, Dorzolamide HCl, Epinastine HCl, Erythromycin, Gancicylovir, Gatifloxacin, Gentamicin Sulfate, Ketorolac Tromethamine, Labetalol, Latanoprost, Loteprednol Etabonate, Moxifloxacin HCl, Nepafenac, Ofloxacin, Olopatadine HCl, Penicillin, Pindolol, Prednisolone, Propanolol, Polymyxin B Sulfate/Trimethoprim Sulfate, Sulfacetamide Sodium, Timolol Maleate, Triflourodine, Tobramycin, Travoprost, Vancomycin, or a mixture of any two or more thereof. In some embodiments, the active pharmaceutical ingredient is Cyclosporine. In some embodiments, the half-cylinder is formed by splitting length-wise a rod (or cylinder) of the cellulose polymer into two substantially equal portions. In some embodiments, a Lacrisert is split in two equal or unequal portions to form the half-cylinder. In some embodiments, the solution includes an alcoholic solvent, such as methanol, ethanol and the like. Other polar or non-polar organic solvents, aqueous solutions and mixtures thereof may be useful in dissolving the active pharmaceutical ingredient of interest, prior to contacting the solid cellulose polymer with the solution comprising the active pharmaceutical ingredient.

In another aspect, an ocular delivery device is provided including a solid, shaped, cellulose polymer, and a therapeutically effective amount of an active pharmaceutical ingredient dispersed in the polymer. In some embodiments, the active pharmaceutical ingredient is selected from Acebutolol, Acyclovir, Betaxolol, Bimatoprost, Brimonidine Tartrate, Brinzolamide, Bromfenac Sodium, Cefazolin, Cephalexin, Cephadroxil, Ciprofloxacin, Ciprofloxacin HCl, Cyclosporine, Dexamethasone, Dorzolamide HCl, Epinastine HCl, Erythromycin, Gancicylovir, Gatifloxacin, Gentamicin Sulfate, Ketorolac Tromethamine, Labetalol, Latanoprost, Loteprednol Etabonate, Moxifloxacin HCl, Nepafenac, Ofloxacin, Olopatadine HCl, Penicillin, Pindolol, Prednisolone, Propanolol, Polymyxin B Sulfate/Trimethoprim Sulfate, Sulfacetamide Sodium, Timolol Maleate, Triflourodine, Tobramycin, Travoprost, Vancomycin, or a mixture of any two or more thereof. In some embodiments, the active pharmaceutical ingredient is selected from Bimatoprost, Brimonidine Tartrate, Brinzolamide, Bromfenac Sodium, Cyclosporine, Dorzolamide HCl, Epinastine HCl, Gatifloxacin, Gentamicin Sulfate, Ketorolac Tromethamine, Latanoprost, Loteprednol Etabonate, Moxifloxacin HCl, Nepafenac, Ofloxacin, Olopatadine HCl, Travoprost, Vancomycin, or a mixture of any two or more thereof. In some embodiments, the polymer comprises more than 30 wt % hydroxypropyl cellulose. In other embodiments, the polymer consists essentially of hydroxypropyl cellulose. In some embodiments, the ocular delivery device is not suspended in an ointment or a liquid. Within these embodiments, in some embodiments, the ocular device is packaged and inserted to the eye, as such.

In another aspect, an ocular delivery device is provided including, a solid, shaped, cellulose polymer, and a therapeutically effective amount of an active pharmaceutical ingredient dispersed in the polymer. In some embodiments, the solid, shaped, cellulose polymer has a surface area to volume ratio of greater than about 4, or greater than about 5, or greater than about 6, or greater than about 7, or greater than about 8, or greater than about 9, or greater than about 10. In some embodiments, the solid, shaped, cellulose polymer has a surface area to volume ratio of from about 4 to about 10, from about 5 to about 10, from about 5 to about 9, from about 4 to about 8, from about 4 to about 7, from about 5 to about 7, from about 4 to about 6, or from about 5 to about 6. As used herein, the unit of length for measuring the surface area and the volume is the same.

In another aspect, an ocular delivery device is provided, which includes a half-cylinder of a cellulose polymer and an active pharmaceutical ingredient dispersed therein. In some embodiments, the active pharmaceutical ingredient is Acebutolol, Acyclovir, Betaxolol, Bimatoprost, Brimonidine Tartrate, Brinzolamide, Bromfenac Sodium, Cefazolin, Cephalexin, Cephadroxil, Ciprofloxacin, Ciprofloxacin HCl, Cyclosporine, Dexamethasone, Dorzolamide HCl, Epinastine HCl, Erythromycin, Gancicylovir, Gatifloxacin, Gentamicin Sulfate, Ketorolac Tromethamine, Labetalol, Latanoprost, Loteprednol Etabonate, Moxifloxacin HCl, Nepafenac, Ofloxacin, Olopatadine HCl, Penicillin, Pindolol, Prednisolone, Propanolol, Polymyxin B Sulfate/Trimethoprim Sulfate, Sulfacetamide Sodium, Timolol Maleate, Triflourodine, Tobramycin, Travoprost, Vancomycin, or a mixture of any two or more thereof. In some embodiments, the ocular delivery device includes a therapeutically effective amount of the active pharmaceutical ingredient. In some embodiments, the half-cylinder is prepared by dividing a rod length-wise in equal, or unequal portions. In some embodiments, the active pharmaceutical ingredient is Cyclosporine.

In another aspect, a method of treating an eye disorder includes depositing one or more of an ocular delivery device having an active pharmaceutical ingredient into the cul-de-sac of the lower eyelid of subject in need thereof. In some embodiments, the eye disorder includes a corneal infection. In some embodiments, the corneal infection includes bacterial keratitis. In some embodiments, the active pharmaceutical ingredient includes a mixture of Vancomycin and Tobramycin.

Within the various aspects and embodiments of the present invention, in some embodiments, the therapeutically effective amount of the API included in an ocular delivery device of the present invention is about 1 µg to about 7.5 mg, about 5 µg to about 5 mg, about 10 µg to about 1 mg, about 20 µg to about 500 µg, or about 50 µg to about 250 µg.

A skilled artisan will appreciate upon reading this disclosure that, just as various APIs are useful in accordance with the present invention, pharmaceutically acceptable salts of certain of these APIs, and free base forms of certain of these APIs are also useful in accordance with the present invention.

In some embodiments, the fraction administered by an ocular delivery device provided herein exceeds that administered by an eye drop. As used herein, the "fraction" is the ratio of the amount of the active pharmaceutical ingredient retained in eye tissues after completion of administration and the total amount of the active pharmaceutical ingredient in the ocular delivery device or the eye drop. When the same amounts of the active pharmaceutical ingredient are used in the ocular delivery device and the eye drop, the fraction may simply be expressed by the respective amounts retained in the eye tissues. For example, the fraction or the amount of drug administered to various tissues of an eye using an ocular delivery device of the invention is about 10%, about 20%, about 30%, about 50%, about 60%, about 70%, or about 80% more than that administered by an eye drop. The fraction may be determined using a variety of methods, including, without limitation, using radioisotopically labeled active pharmaceutical ingredients, as disclosed hereinbelow. The comparative eye drops may be available commercially or easily formulated by the skilled artisan using known components and following known procedures.

DETAILED DESCRIPTION

Figure 1:
FIG. 1 is a photograph of a plain, unloaded Lacrisert® (A) and Lacriserts® after being loaded with fluorescently labeled Vancomycin and dried (B-D).

Provided herein are ocular delivery devices, methods of forming the ocular delivery devices, and methods of using the ocular delivery devices.

Methods of Forming the Ocular Delivery Devices

The disclosed methods of forming ocular delivery devices involve exposing a solid, shaped cellulose polymer to a solution containing an API and a solvent capable of solubilizing the API. During this step, the polymer absorbs at least a portion of the solution, including the API and solvent, thereby becoming loaded with the API. The methods further include removing at least a portion of the absorbed solvent from the polymer by allowing the absorbed solvent to evaporate from the polymer or by drying the polymer. Various amounts of the absorbed solvent may be removed from the polymer. In some embodiments, at least 10% of the absorbed solvent is removed. This includes embodiments in which at least 30%, 50%, 70%, 90%, or more of the absorbed solvent is removed from the polymer. In still other embodiments, substantially all of the absorbed solvent is removed. By "substantially all," it is meant that nearly all of the absorbed solvent is removed from the polymer, such that it would be recognized by those of skill in the art as being dry, although every single molecule of solvent may not necessarily be removed.

Allowing the absorbed solvent to evaporate from the polymer may be accomplished by a variety of means. By way of example only, the polymer may simply be exposed to the ambient environment for a period of time until the desired amount of solvent has evaporated from the polymer. Similarly, a variety of techniques may be used to actively dry the polymer after it has absorbed the API-containing solution. By way of example only, the polymer may be placed in a vacuum oven for a period of time. The drying may be carried out at a variety of temperatures and pressures for a variety of periods of time. In some embodiments, the drying is carried out at room temperature. In other embodiments, the drying is carried out above room temperature. In yet other embodiments, the drying is carried out at a temperature from about 20° C. to about 79° C. In some embodiments, the drying is carried out from about 30° C. to about 40° C. In some embodiments, the drying is carried out under a vacuum from about 0.1 to about 20 psi, In some embodiments, the drying is carried out for at least 30 seconds, at least 1 minute, at least 10 minutes, at least 20 minutes, at least 30 minutes, at least 45 minutes, at least one hour, at least two hours, at least three hours, at least five hours, or at least ten hours. In some embodiments, the drying is carried out from about 10 minutes to about 5 days, about 10 minutes to about 24 hours, from about 10 minutes to 12 hours, from about 10 minutes to 10 hours, from about 10 minutes to 8 hours, about 10 minutes to 7 hours, about 10 minutes to 6 hours, about 10 minutes to 5 hours, about 10 minutes to 4 hours, about 10 minutes to 3 hours, about 30 minutes to 8 hours, about 30 minutes to 7 hours, about 30 minutes to 6 hours, about 30 minutes to 5 hours, about 30 minutes to 4 hours, about 30 minutes to 3 hours, about 1 hour to about 15 hours, about 1 hour to 12 hours, about 1 hour to 8 hours, about 1 hour to 5 hours, or about 1 hour to about 3 hours. In other embodiments, the drying is carried out for about 12 hours, about 10 hours, about 8 hours, about 7 hours, about 6 hours, about 5 hours, about 4 hours, about 3 hours, about 2 hours, about 1 hour, about 45 minutes, about 30 minutes, about 15 minutes, about 10 minutes, about 9 minutes, about 8 minutes, about 7 minutes, about 6 minutes, about 5 minutes, about 4 minutes, about 3 minutes, about 2 minutes, about 1 minute, or about 30 seconds. In still other embodiments the drying is carried out overnight, preferably, under sterile conditions.

In some embodiments, the methods further include placing the polymer in a vessel prior to exposing the polymer to the API-containing solution. Absorption of the solution by the polymer may cause the polymer to swell, thereby increasing its dimensions and distorting its shape. The vessel may be adapted to restrict the swelling of the polymer in at least one direction, in more than one direction, or in all directions of the polymer. By "adapted" it is meant that the interior surface of the vessel has a shape and dimensions sufficient to restrain the swelling of the polymer in a particular direction of the polymer. In some embodiments, the shape and dimension of an interior surface of the vessel substantially matches the shape and dimension of an exterior surface of the polymer. By "substantially matches" it is meant that the shapes and dimensions of the interior surface of the vessel and the exterior surface of the polymer are similar, but not necessarily identical. Restriction of the shape prevents the polymer from flowing.

A variety of vessels having a variety of shapes and dimensions may be used, depending upon the shape and dimensions of the polymer. In some embodiments, the vessel is a tubular vessel. By way of example only, a tubular vessel may be used to restrict the swelling of a rod-shaped polymer. A tubular vessel having an inner diameter that substantially matches the outer diameter of the rod-shaped polymer is capable of restricting the radial swelling of the polymer as it absorbs solution. The inner length of the tubular vessel may, but need not, substantially match the outer length of the rod-shaped polymer. If the inner length of the tubular vessel does not substantially match the outer length of the rod-shaped polymer, the polymer may be allowed to swell in the longitudinal direction as the polymer absorbs solution. In another embodiment, the vessel can be shaped to accept a disc-shaped polymer. The vessel can have one or more perforations to allow drug solution to permeate the polymer contained within the vessel. Non-limiting examples of vessels that are inexpensive and readily available are pipette tips and glass or plastic tubes.

For those embodiments including the use of a vessel, the methods may further include freeing the polymer from the vessel. In some embodiments, the drug-loaded polymer may readily move from the vessel, or may be forced out. In other embodiments, the interior surface of the vessel may be coated with a release agent to facilitate the freeing of the polymer from the vessel. A variety of release agents may be used, depending upon the composition of the polymer and the composition of the vessel. Suitable release agents include, but are not limited to silanizing agents. For example, a plastic or glass tube may be coated with a silanizing agent that will readily release from the polymer after drug-loading. Silanizing agents are well known in the art and examples include, but are not limited to isocyanato-γ-propyltrimethoxysilane, 3-(acryloxypropyl)trichlorosilane, 3-aminopropyltriethyoxysilane, 3-aminopropyltrimethoxysilane, (3-glycidoxypropyl)trimethoxysilane, (3-glycidoxypropyl)-triethoxysilane, (3-mercaptopropyl)triethoxysilane, and (3-mercaptopropyl)-trimethoxysilane. Finally, when vessels are used, the polymer may remain in the vessel during the evaporation or drying step.

In some embodiments, the formed ocular delivery device is capable of releasing the absorbed API upon exposure of the ocular delivery device to a liquid medium. In some such embodiments, the medium includes tear fluid. The tear fluid may be from an animal, including a human, a primate, a rabbit, a dog, a cat, a horse, a cow, a pig, a guinea pig, a rat, or a mouse. In some embodiments, the tear fluid is human tear fluid or a buffered medium. The period of time over which the absorbed API is released may vary. In some embodiments, the ocular delivery device releases the absorbed API over a period of about ½ hour to about 72 hours. This includes embodiments in which the absorbed API is released over a period of about 2 hours to about 60 hours, about 2 hours to about 48 hours, about 2 hours to about 36 hours, about 2 hours to about 24 hours, about 2 hours to about 20 hours, about 2 hours to about 15 hours, or about 2 hours to about 12 hours. However, other time periods are possible. In some embodiments, the release of the API from the polymer is substantially uniform. By "substantially uniform," it is meant that the rate of release of API from the polymer is nearly constant over any of the time periods described above, although the rate of release may not be exactly constant. In some embodiments, the release rate is increased in the initial time periods after insertion (i.e. a dumping of the drug occurs initially), followed by a substantially uniform, or substantially zero-order, release rate, for intermediate time periods following insertion, followed by a decreasing release rate at the later time periods following insertion. For example, in the first one or two hours after insertion of the drug-loaded insert into the eye, dumping of the drug from the insert occurs, followed by a substantially zero-order release rate over hours 1, 2, or 3 through 6, followed by a decreasing release rate after hours 6 or 7.

As noted above, the disclosed methods involve forming ocular delivery devices from solid, shaped cellulose polymers. A variety of cellulose polymers may be used, including, but not limited to hydroxymethyl cellulose, hydroxyethyl cellulose, hydroxypropyl cellulose, hydroxypropylmethyl cellulose, or a mixture of any two or more thereof. In some embodiments, the polymer includes hydroxypropyl cellulose. In some such embodiments, the polymer includes more than 30% hydroxypropyl cellulose. In yet other such embodiments, the polymer consists essentially of hydroxypropyl cellulose.

The cellulose polymers used in the disclosed methods are characterized by being in the solid phase and by having a particular shape. The shape and dimension of the solid polymers is not particularly limited provided that the polymer may be inserted into a subject's eye while minimizing irritation and/or damage to the eye given the size of the insert. The polymers may have a variety of shapes, including, but not limited to rods, rectangles, discs, and the like. Suitable dimensions of the polymers are those that provide a surface area ranging from about 0.1 mm$^2$ to about 200 mm$^2$. However, other surface areas are possible. Methods for forming the solid, shaped cellulose polymers are known.

In some embodiments, the shape of the ocular insert device has a length from about 1 mm to about 8 mm, about 1 mm to about 7 mm, about 1 mm to about 6 mm, about 1 mm to about 5 mm, about 1 mm to about 4 mm, about 1 mm to about 3 mm, about 1 mm to about 2.5 mm, about 1.5 mm to about 8 mm, about 1.5 mm to about 7 mm, about 1.5 mm to about 6 mm, about 2 mm to about 8 mm, about 2 mm to about 7 mm, or about 2 mm to about 6 mm, about 1.5 mm to about 5, about 1.5 mm to about 4 mm, about 2 mm to about 3 mm, and about 1.5 mm to about 2.5 mm. In some embodiments, the shape of the ocular insert device has a width from about 1 mm to about 3.5 mm, about 1 mm to about 2 mm, about 1 mm to about 1.5 mm, about 1.2 mm to about 3 mm, about 1.5 mm to about 2 mm, about 1.2 mm to about 1.5 mm, about 1.3 mm to about 3 mm, about 1.3 mm to about 2 mm, or about 1.3 mm to about 1.5 mm. In some embodiments, the shape approximates a cylinder and the width is a diameter.

In some embodiments, the dimensions and or shape of the insert are distorted as compared to an insert that is not loaded with an API. Such distortions may be expressed through the surface area to volume ratio. A typical, Lacrisert®, without any API has a surface area to volume ratio of approximately 3.9. Thus, in some embodiments, the solid, shaped, cellulose polymer has a surface area to volume ratio of greater than about 4, or greater than about 5, or greater than about 6, or greater than about 7, or greater than about 8, or greater than about 9, or greater than about 10. In other embodiments, the solid, shaped, cellulose polymer has a surface area to volume ratio of from about 4 to about 10, from about 4 to about 9, from about 4 to about 8, from about 4 to about 7, from about 4 to about 6, from about 4 to about 5, from about 5 to about 10, from about 5 to about 9, from about 5 to about 8, from about 5 to about 7, or from about 5 to about 6. Such an increase in surface area to volume may allow for greater surface area contact with tears or another medium, thereby increasing or modulating the drug delivery rate from the ocular delivery device.

In the disclosed methods, the solid, shaped cellulose polymers are exposed to a solution having an API and a solvent. A variety of APIs may be used, such as those useful for treating or preventing an eye disorder. Exemplary eye disorders are described below. In some embodiments, the API is an API that is thermally unstable above about 40° C., about 50° C., about 60° C., about 70° C., about 80° C., about 100° C., about 200° C., or about 300° C. These are temperatures that are typically used during conventional polymer molding processes such as compression molding, injection molding, or extrusion. Thus, in some embodiments, the API is one that is unstable at injection molding or extrusion temperatures.

APIs include, but are not limited to antibiotics, antibacterials, antivirals, anti-allergenics, non-steroidal anti-inflammatories, steroidal anti-inflammatories, decongestants, miotics, anti-cholinesterases, mydriatics, sympathomimetics, and β-blockers. Non-limiting examples of APIs include Acebutolol, Acyclovir, Betaxolol, Bimatoprost, Brimonidine Tartrate, Brinzolamide, Bromfenac Sodium, Cefazolin, Cephalexin, Cephadroxil, Ciprofloxacin, Ciprofloxacin HCl, Cyclosporine, Dexamethasone, Dorzolamide HCl, Epinastine HCl, Erythromycin, Gancicylovir, Gatifloxacin, Gentamicin Sulfate, Ketorolac Tromethamine, Labetalol, Latanoprost, Loteprednol Etabonate, Moxifloxacin HCl, Nepafenac, Ofloxacin, Olopatadine HCl, Penicillin, Pindolol, Prednisolone, Propanolol, Polymyxin B Sulfate/ Trimethoprim Sulfate, Sulfacetamide Sodium, Timolol Maleate, Triflourodine, Tobramycin, Travoprost, Vancomycin, or a mixture of any two or more thereof. Other non-limiting examples of APIs include Azelastine HCl, Atropine sulfate, Betamethasone, Carbachol, Pheniramine, Cromolyn sodium, Cyclopentolate, Demecarium bromide, Dexamethasone 21-phosphate, Erythromycin Base, Fluorometholone, Gatifloxacin, Homatropine, Hydroxyamphetamine, Idoxuridine, Medrysone, Methylprednisolone, Naphazoline, Resolvins, Phospholipids, Phenylephrine, Pholoxaline iodide, Prednisolone Acetate, Prednisolone Sodium Sulfate, Sulfisoxazole, Tetrahydrazoline HCl, Timolol, Tobramycin Sulfate, Tropicamide, 6-hydroxy-2-sulfamoylbenzo[b]thiophene, 6-acetoxy-2-sulfamoylbenzo[b]thiophene, 5,6-dihydro-4H-4-hydroxythieno[2,3-b]thiopyran-2-sulfonamide-7,7-dioxide, or a mixture of any two or more thereof. In some embodiments, the API is Vancomycin. In some embodiments, the API is Cyclosporine. In other embodiments, the API is a mixture of Vancomycin and Tobramycin.

Similarly, a variety of solvents may be used. In fact, the solvent is not particularly limited provided the solvent is capable of solubilizing the desired API. The phrase "capable of solubilizing" is meant to include those solvents that completely solubilize and those that partially solubilize the desired API. An exemplary solvent is water. However, organic solvents may be used, including, but not limited to methanol, ethanol, n-propanol, iso-propanol, n-butanol, iso-butanol, tert-butanol, dimethyl ether, methylethyl ether, methyl-tert-butyl ether, diethyl ether, ethylene glycol, propylene glycol, dioxane, dimethyl sulfoxide, dimethyl formamide or mixtures of any two or more such solvents. The only limitation regarding the solvent is that it be susceptible to being dried from the polymer by evaporation or vacuum. In some embodiments, the solvent is deionized water or a buffered system.

The concentration of the API in the solution may vary. In fact, the concentration is not particularly limited and may be chosen depending upon the volume of the solution used to expose the polymer, the desired amount of API to be absorbed by the polymer, and the maximum amount of API that can be absorbed by the polymer before saturation. The desired amount of API may be that amount which provides a desired therapeutic effect in a subject treated with the ocular delivery device. Since the desired amount of API to be absorbed depends upon at least the nature of the eye disorder, the subject's characteristics (e.g., the subject's age, body weight, general health, sex, and diet) and the desired dosing regimen, and since the amount of API that can be absorbed depends upon at least the type of API and the type and dimensions of the polymer, it is not practical to provide specific concentration ranges. However, suitable concentrations of API may be readily determined by taking into consideration these and other factors. In addition, the Examples below provide an exemplary concentration when Lacrisert is used as the polymer, Vancomycin is used as the API, and the disorder to be treated is a *S. aureus* infection.

As described above, the disclosed methods involve a step of exposing the polymer to an API-containing solution (i.e., a "load" or "loading" step) and a step of removing at least a portion of the absorbed solvent from the polymer (i.e., an "evaporation" or "drying" step). The methods may further involve repeating these steps to load the polymer with additional API, or a different API. In other words, the methods may involve one or more load steps and one or more evaporation or dry steps. By way of example only, in one embodiment, the method includes a first step of exposing the polymer to a first solution having an API and a solvent, a second step of allowing the absorbed solvent from the first solution to evaporate from the polymer or drying the polymer, a third step of exposing the polymer to a second solution having an API and a solvent, and a fourth step of allowing the absorbed solvent from the second solution to evaporate from the polymer or drying the polymer. Each of these steps may be repeated. In another non-limiting example, the method may include multiple load steps and one or more dry steps. In other words, there need not be a dry step for every load step and the order of the dry step may vary.

Ocular Delivery Devices

Also provided are ocular delivery devices formed from any of the methods described above. The ocular delivery devices include a solid, shaped cellulose polymer and a therapeutically effective amount of an API dispersed in the polymer. By "therapeutically effective amount" it is meant that amount which results in a desired therapeutic effect for a particular eye disorder. As further described below, a desired therapeutic effect may be the alleviation, in whole or in part, of symptoms associated with the eye disorder; the halting of further progression or worsening of those symptoms; or the prevention of the eye disorder. As described above, the amount needed to achieve these effects may be readily determined by considering the relevant factors (e.g., nature of the eye disorder, the subject's characteristics, dosing regimen, etc.). Any of the cellulose polymers or APIs described above may be used in the devices. Similarly, the devices may possess any of the characteristics described above.

The disclosed ocular delivery devices are distinguished from conventional ocular delivery devices in a number of ways. By way of example only, the disclosed devices may include particular APIs that would not be typically found in polymeric ocular inserts because the APIs are incompatible with the conventional methods of forming such inserts. These conventional methods include, but are not limited to, compression molding, injection molding, and extrusion, each of which requires relatively high processing temperatures and film casting, which may require elevated temperatures (80° C. and above) and a solvent that is capable of dissolving both the polymer and the API. Thus, in some embodiments, the API in the ocular delivery device is selected from Acebutolol, Acyclovir, Betaxolol, Bimatoprost, Brimonidine Tartrate, Brinzolamide, Bromfenac Sodium, Cefazolin, Cephalexin, Cephadroxil, Ciprofloxacin, Ciprofloxacin HCl, Cyclosporine, Dexamethasone, Dorzolamide HCl, Epinastine HCl, Erythromycin, Gancicylovir, Gatifloxacin, Gentamicin Sulfate, Ketorolac Tromethamine, Labetalol, Latanoprost, Loteprednol Etabonate, Moxifloxacin HCl, Nepafenac, Ofloxacin, Olopatadine HCl, Penicillin, Pindolol, Prednisolone, Propanolol, Polymyxin B Sulfate/Trimethoprim Sulfate, Sulfacetamide Sodium, Timolol Maleate, Triflourodine, Tobramycin, Travoprost, Vancomycin, or Cyclosporine, or a mixture of any two or more thereof. Plus Azelastine HCl, Atropine sulfate, Betamethasone, Carbachol, Pheniramine, Cromolyn sodium, Cyclopentolate, Demecarium bromide, Dexamethasone 21-phosphate, Erythromycin Base, Fluorometholone, Gatifloxacin, Homatropine, Hydroxyamphetamine, Idoxuridine, Medrysone, Methylprednisolone, Naphazoline, Resolvins, Phospholipids, Phenylephrine, Phospholine iodide, Prednisolone Acetate, Prednisolone Sodium Sulfate, Sulfisoxazole, Tetrahydrazoline HCl, Timolol, Tobramycin Sulfate, Tropicamide, 6-hydroxy-2-sulfamoylbenzo[b]thiophene, 6-acetoxy-2-sulfamoylbenzo[b]thiophene, 5,6-dihydro-4H-4-hydroxythieno[2,3-b]thiopyran-2-sulfonamide-7,7-dioxide, or a mixture of any two or more thereof. In other embodiments, the API is Vancomycin. In some embodiments, the API is Cyclosporine. In still other embodiments, the API is a mixture of Vancomycin and Tobramycin.

As another non-limiting example, the cellulose polymer of the disclosed devices may include a substantial amount of hydroxypropyl cellulose. Such devices are distinguished from conventional devices which seek to limit the amount of hydroxypropyl cellulose because of the potential for this polymer to cause blurred vision. In some embodiments, the polymer includes more than 30% hydroxypropyl cellulose. In other embodiments, the polymer consists essentially of hydroxypropyl cellulose.

In other embodiments, the disclosed ocular delivery device is not suspended in a liquid or ointment. Such devices are distinguished from conventional devices which, due to a variety of limitations, such as size, may be required to be delivered to a subject in a liquid or ointment vehicle.

Finally, in the disclosed ocular delivery devices, the polymer has been exposed to a solution comprising the API and a solvent capable of solubilizing said API and further, the absorbed solvent has been allowed to evaporate from the polymer or the polymer has been dried to remove the absorbed solvent. Consequently, the polymers of the disclosed devices have been "pre-swollen," which results in a faster dissolution of the polymer in a medium, including tear fluid. In some embodiments, the polymer of the disclosed devices dissolves faster than if the polymer had not been pre-swollen. In some such embodiments, the dissolution is 1.5 times, 2 times, 3 times, 5 times faster, or even more.

Methods of Using the Ocular Delivery Devices

Methods of using the ocular delivery devices include treating an eye disorder by depositing any of the disclosed ocular delivery devices into or onto an eye of a subject in need thereof. In a particular embodiment of the invention, the ocular delivery device is placed, inserted, or deposited, into the inferior cul-de-sac of the eye. By "treating," it is meant alleviating, in whole or in part, symptoms associated with an eye disorder; halting of further progression or worsening of those symptoms; or preventing the development of the eye disorder. For example, in treating an eye disorder, the prevention of, reduction of, or elimination of the disorder are examples of desirable therapeutic effects. Finally, treating does not necessarily occur by administration of one ocular delivery device, but may occur upon administration of a series of ocular delivery devices over a specified period of time.

The disclosed devices may be used to treat a variety of eye disorders or traumas, and a variety of subjects. Eye disorders may include infections caused by bacteria or viruses, surgical procedures, and eye diseases such as glaucoma, ocular melanoma, retinitis pigmentosa, elevated intraocular pressure, photoreceptor degeneration, intraocular neovascularization, vitreoretinopathy, retinal degeneration, retinal ischemia, retinal neovascularization, retinal pigment epithelium disease, dry eye syndrome, seasonal allergies, and trachoma. In some embodiments, the dry eye syndrome comprises meibumium gland dysfunction and aqueous deficient dry eye. Eye disorders may also include post-surgical periods where healing and/or infections may be a concern. By way of example only, the eye disorder may include a corneal infection. The corneal infection may include viral or bacterial keratitis. The subjects include any animal that can benefit from the administration of the disclosed devices. In some embodiments, the subject is a mammal (e.g., a human, a rabbit, a primate, a dog, a cat, a horse, a cow, a pig, a rat, or mouse). In some such embodiments, the subject is a human.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

The use of the terms "a" and "an" and "the" and similar referents in the context of describing the elements (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential to the practice of the invention.

As used herein, "about" will be understood by persons of ordinary skill in the art and will vary to some extent depending upon the context in which it is used. If there are uses of the term which are not clear to persons of ordinary skill in the art, given the context in which it is used, "about" will mean up to plus or minus 10% of the particular term.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Additionally the phrase "consisting essentially of" will be understood to include those elements specifically recited and those additional elements that do not materially affect the basic and novel characteristics of the claimed invention. The phrase "consisting of" excludes any element not specifically specified. In addition, where features or aspects of the disclosure are described in terms of Markush groups, those skilled in the art will recognize that the disclosure is also thereby described in terms of any individual member or subgroup of members of the Markush group.

The present invention, thus generally described, will be understood more readily by reference to the following examples, which are provided by way of illustration and are not intended to be limiting of the present invention.

EXAMPLES

Example 1. Absorption and Release of API by a Solid, Shaped Hydroxypropyl Cellulose Polymer Materials: Fluorescently labeled Vancomycin (FVanc) was used as the API. Lacrisert® from Aton Pharma, Inc. (Lawrenceville, N.J., USA) was used as the solid, shaped cellulose polymer. Lacrisert® is a sterile, semi-translucent to opaque, rod-shaped (diameter~1.27 mm, length~3.5 mm), water soluble, ophthalmic insert made of hydroxypropyl cellulose for administration into the inferior cul-de-sac of the eye. Each Lacrisert® included 5 mg of hydroxypropyl cellulose and contained no preservatives or other ingredients. Micropipette tips were used as a vessel to restrict the swelling of the polymer.

FVanc was dissolved in deionized water at 50 mg/mL. A single Lacrisert® was placed into a pipette tip, blocking the tip. Twenty-five μL of the FVanc solution was added to the pipette tip. The Lacrisert® absorbed the FVanc solution within minutes. Although the Lacrisert® swelled as it absorbed the solution, the pipette restricted the swelling of the polymer in the radial direction. The pipette containing the swollen Lacrisert® was placed in a vacuum oven at room temperature for about 3 hours. After drying, the drug loaded Lacrisert® was removed from the pipette tip by cutting the end of the pipette tip and releasing the Lacrisert®. FIGS. 1A-1D show and unloaded Lacrisert® (A), and FVanc loaded and dried Lacriserts® (B-D), having varying drying times. The Lacrisert® shown in FIG. 1B was used for the release study described immediately below.

Figure 2:
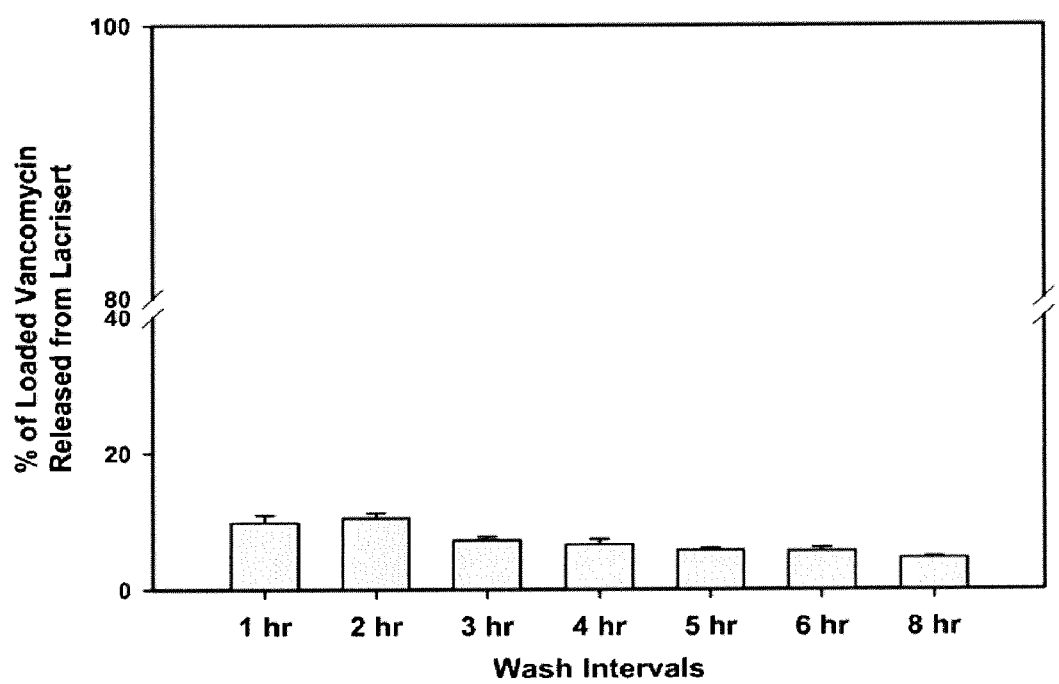
FIG. 2 shows the results of a study of the release of fluorescently labeled Vancomycin (FVanc) from Lacrisert®. As shown in the figure, 50±4% (~625 µg) FVanc was released from the loaded Lacrisert® over an eight hour period.

For the release study, the loaded Lacrisert® was placed into 750 μL of a balanced salt solution (BSS) wash solution and rocked gently at 32° C. in the dark. After an hour, the BSS wash solution was removed, the fluorescence of the BSS wash solution was measured, and the loaded Lacrisert® was exposed to another 750 μL BSS. As shown in FIG. 2, 50±4% (~625 μg) FVanc was released from the loaded Lacrisert® over an eight hour period. Notably, there is a dumping (higher release rate) of the FVanc in the initial time periods, follow by a period of substantial uniform release, before a reduced rate of release at the later time periods.

The amount of FVanc released from the loaded Lacrisert was similar to the amount of API delivered in conventional treatments. Conventional Vancomycin treatments involve delivering to an eye about 8 drops (27 μL per drop) of Fortified Vancomycin (25 mg/mL) over an eight hour period, resulting in the delivery of a total of 5400 μg Vancomycin.

However, about 90% of the treatment exits the tear film via the lacrimal system or onto the patient's cheek before exerting any biological activity. Thus, conventional treatments provide about 540 µg of Vancomycin over an eight hour period.

Example 2. In Vivo Study of API-Loaded Hydroxypropyl Cellulose Polymer

Materials: Vancomycin (Vanc) was used as the API. Lacrisert® from Aton Pharma, Inc. was used as the solid, shaped cellulose polymer. Vanc loaded Lacriserts® were formed as described in Example 1 above.

Five New Zealand white rabbits from a commercial vendor were used. ATCCA 25923, a Vancomycin sensitive strain of *S. aureus*, was used as a model of bacterial keratitis. The following anesthetics or analgesics were used in the study: ketamine (50 mg/kg) at euthanasia and inoculation; ketamine (5 mg/kg) at euthanasia and inoculation; proparacaine (0.5% solution, 1-2 drops) at inoculation; and buprenorphine (0.03 mg/kg) every 8-10 hours. An intracardiac injection of sodium pentobarbital (90 mg/kg) was used as the method of euthanasia.

Rabbit corneas were infected interstromally in the lab using Biosafety Level 2 protocols. An aliquot of bacterial dilution (10 µL, 100 colony forming units (CFUs)) was injected into the corneal stroma of both eyes of each rabbit (a total of ten eyes, five rabbits). Prior to injection, all rabbits were anesthetized by subcutaneous injection of xylazine/ketamine and two drops of proparacaine hydrochloride topically applied to each eye. Post infection, each rabbit received appropriate intramuscular injections of buprenorphine to alleviate any pain or distress caused by the corneal infection. One rabbit was excluded from the study due to an inadvertent cornea perforation.

Twelve hours post-inoculation, each eye was graded by slit lamp examination (SLE) with a slit lamp biomicroscope using a published scoring system. SLE grading was done by a single observer who was blinded to treatment groups. In addition, at this time, either a drug-loaded Lacrisert® or an unloaded, plain Lacrisert® was placed in the precorneal cul de sac of the eye. Of the total of eight eyes studied (four rabbits), two eyes received no treatment at all (control); two eyes received an unloaded, plain Lacrisert®; and four eyes received a drug-loaded Lacrisert®. Eight hours after initiation of treatment (twenty hours post-inoculation), the eyes were reexamined by SLE, the treatment removed, the precorneals washed with BSS, animals sacrificed, and the corneas aseptically removed for colony counting. Harvested corneas were homogenized in phosphate buffered saline (PBS), centrifuged, and eight serial dilutions of the supernatant were performed. Each homogenate and each of the serial dilutions were plated on tryptic soy agar in triplicate and incubated for 48 hours prior to counting CFUs.

Figure 3:
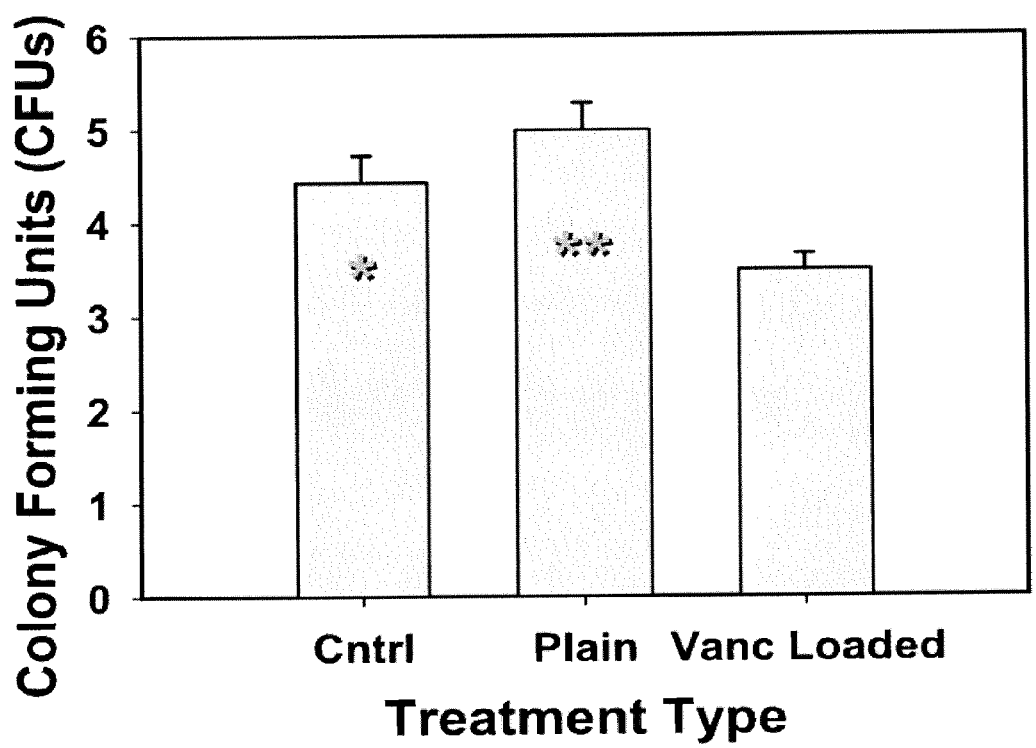
FIG. 3 shows the results of an in vivo study of the effectiveness of Lacrisert® loaded with Vancomycin (Vanc). The figure is a graph of the colony forming units (CFUs) cultured from control corneas (Cntrl), corneas treated with unloaded Lacrisert® (Plain), and corneas treated with Vanc loaded Lacrisert® (Vanc Loaded).
Figure 4:
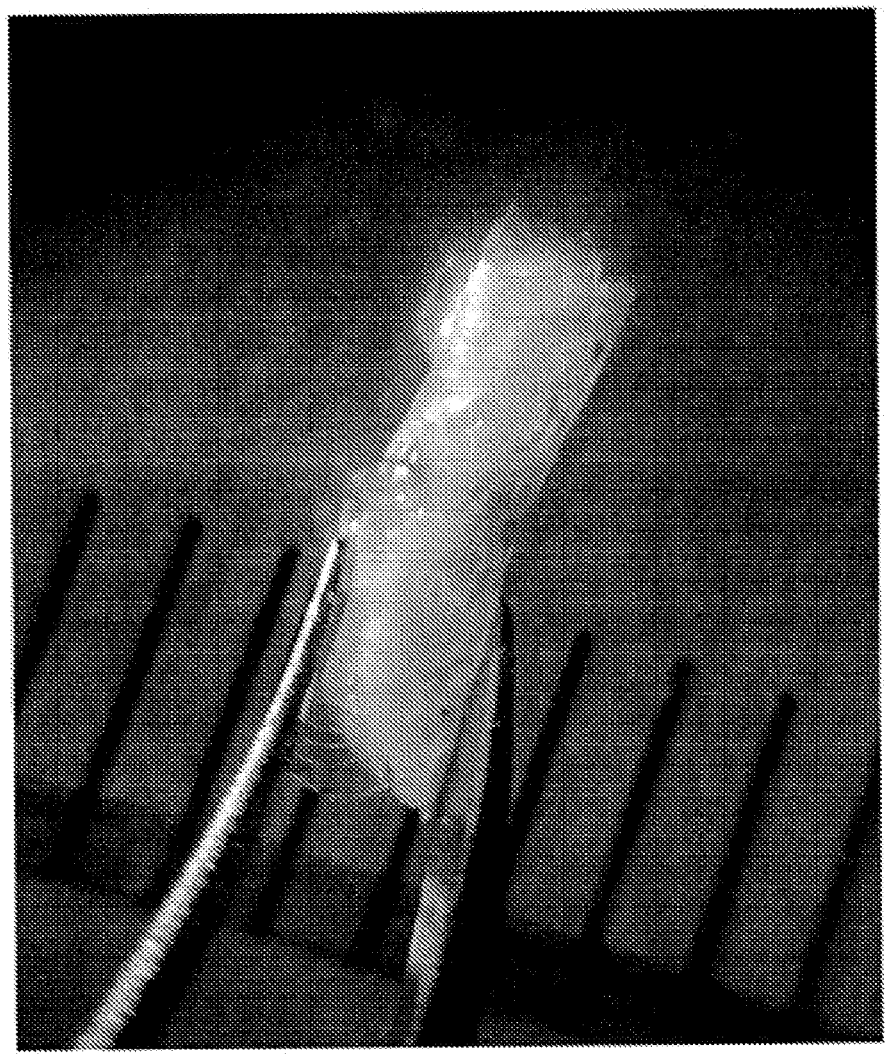
FIG. 4 shows a drug-loaded Lacrisert®, which is about twice as long as commercially available, unloaded Lacrisert®.
Figure 5:
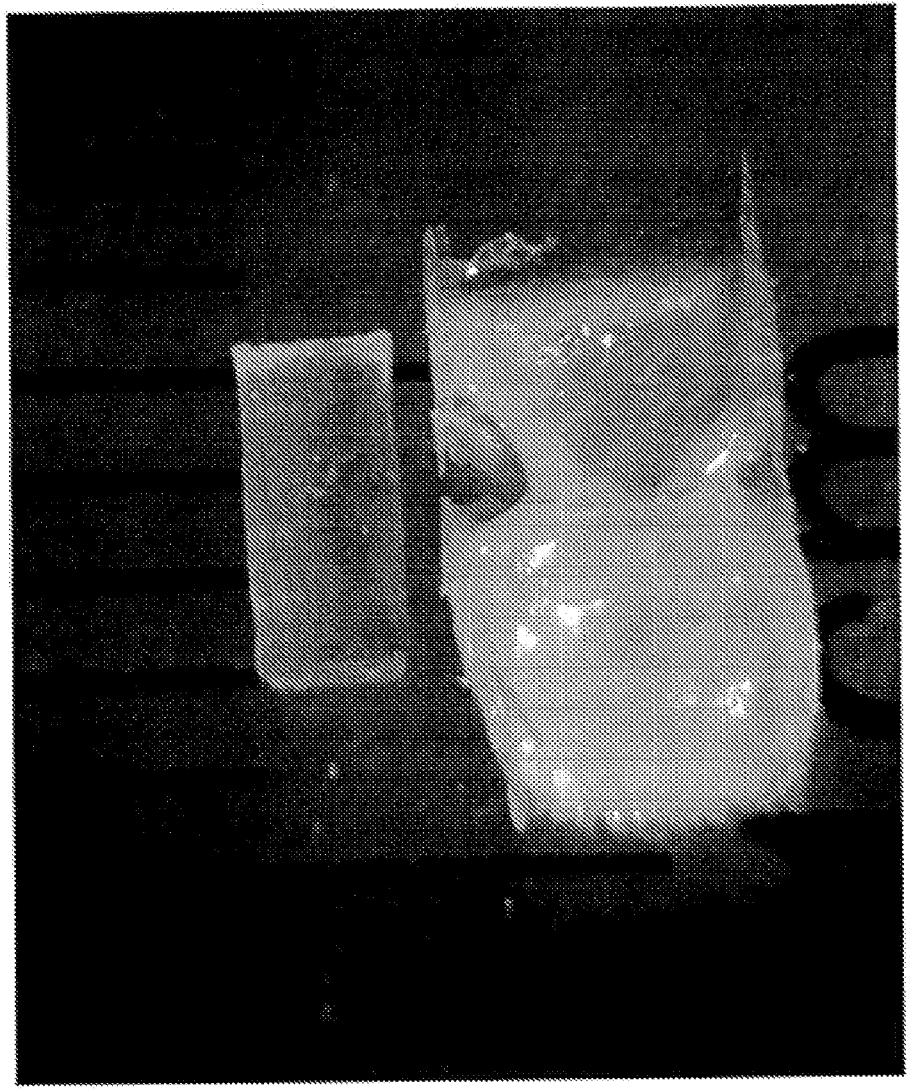
FIG. 5 shows a drug-loaded Lacrisert®, which is rectangularly shaped compared with commercially available, unloaded Lacrisert®.
Figure 6:
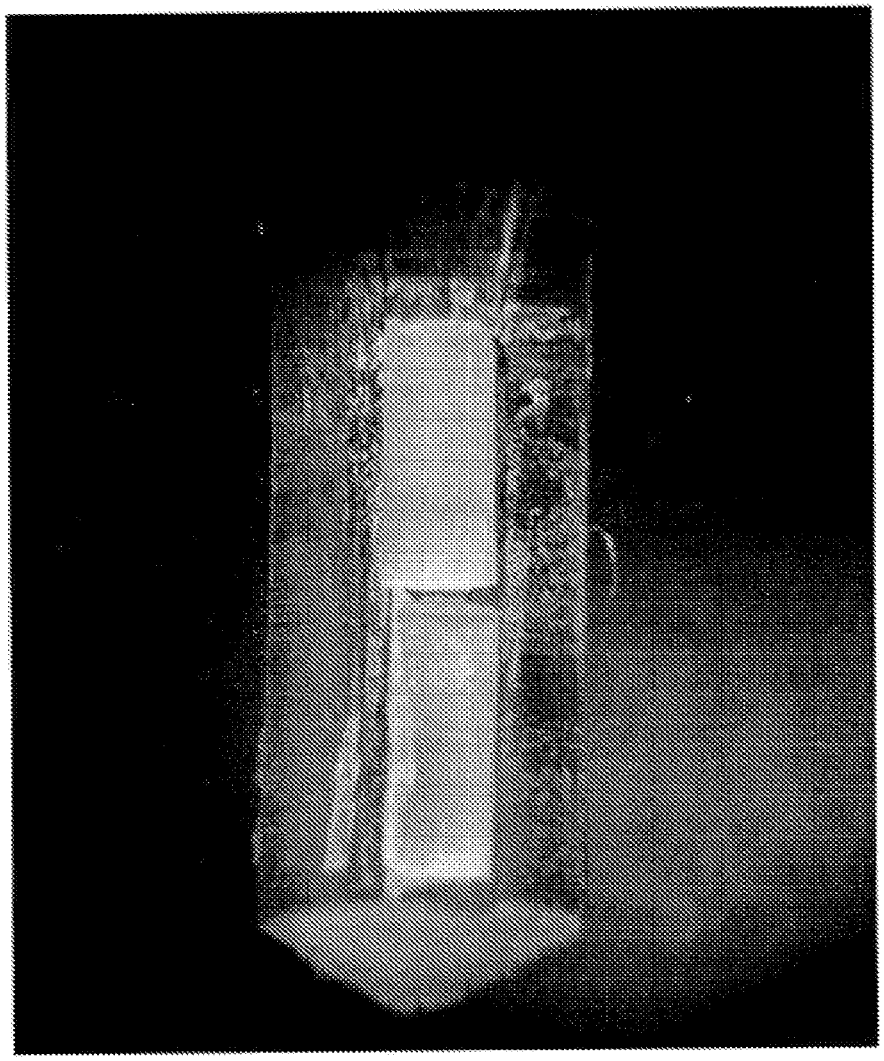
FIG. 6 shows an unloaded Lacrisert®, which has been split length-wise and placed end-to-end in a polymer trough (i.e., the form) made from poly(methylmethacrylate) or PMMA. A solution of drug is then then introduced into the form and absorption takes place. The drug-loaded Lacrisert® can then be dried. The resulting shape can be a half-cylinder or more rectangular in shape. The two halves may also meld together.
Figure 7:
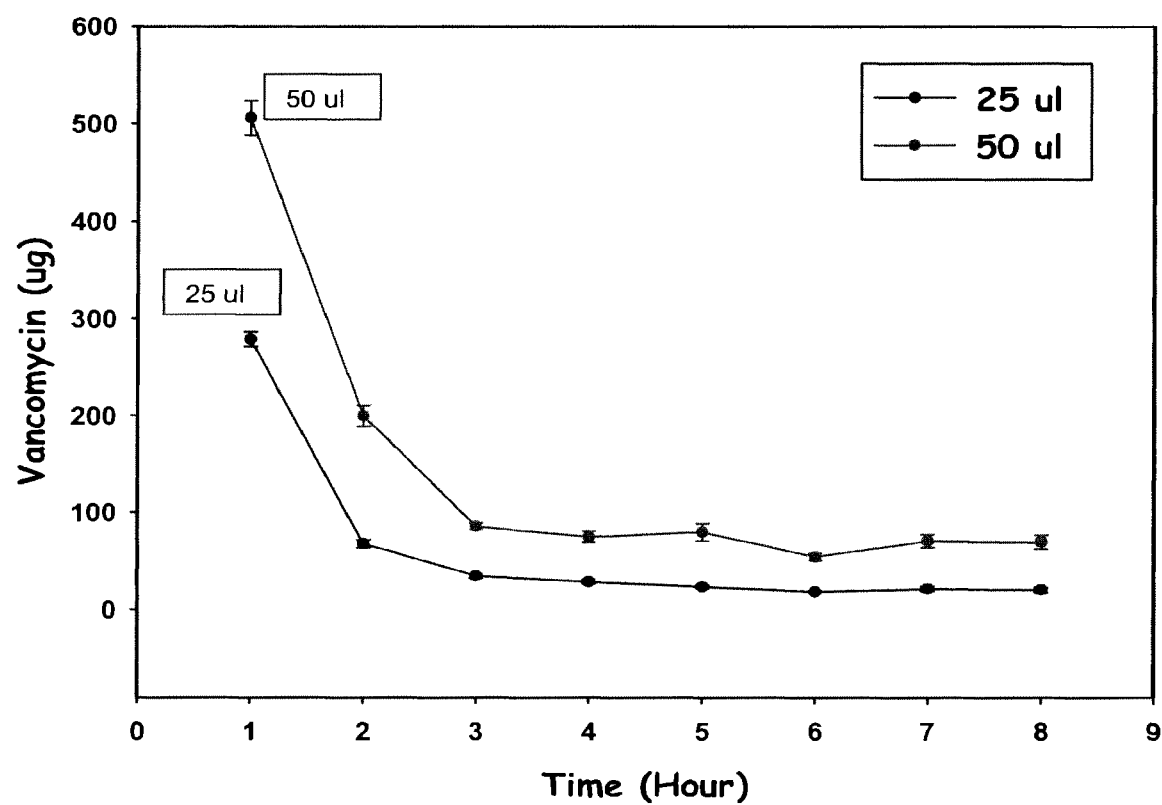
FIG. 7 is a plot of the release rates of two Vanc-loaded cellulose polymers of the invention. One absorbed 25 microliters of a solution of Vanc, and the second absorbed 50 microliters of the same solution of Vanc. That is one device contained twice the amount of Vanc as the other and yet the rate of release can be described as zero-order between Time (hour) 3-8, as shown in the plot.

The results of the cultures are shown in FIG. 3. This figure plots the CFUs cultured from the control corneas (Cntrl), the corneas treated with unloaded Lacrisert® (Plain), and the corneas treated with Vanc-loaded Lacrisert® (Vanc Loaded). The results show that plain Lacriserts® increased the amount of infection present in the eye compared to the control eyes, although the increase was not statistically significant. However, Vanc-loaded Lacriserts® significantly reduced the CFUs of *S. aureus* compared to the control eyes.

Example 3. In Vivo Study of API-Loaded Hydroxypropyl Cellulose Polymer in Animal Models of Eye Disease Lacrisert® or Lacrisert halves from Aton Pharma, Inc. will be used as the solid, shaped cellulose polymer. Lacriserts® will be loaded with a therapeutic agent directed to the treatment of inflammatory eye disease as described in Example 1. Animals modeling human diseases will be selected for uniformity of condition based on an appropriate grading standard and divided into control and experimental groups. Unloaded and drug-loaded Lacriserts® will be administered to control and experimental animals, respectively, by the methods of Example 2. Lacrisert halves will be loaded with a therapeutic agent and applied as a pair as exemplified below. Following an appropriate period of treatment, animals will be subjectively evaluated for the extent of disease regression. The animals will then be euthanized and the relevant tissues examined histologically. Relevant parameters will be tabulated and compared to assess the efficacy of the drug.

Animals used to model human eye diseases include mice, rats, dogs, cats, rabbits, monkeys, pigs, and guinea pigs. Potential diseases that may be modeled include, but are not limited to inflammatory eye diseases, neoplastic disorders, retinitis pigmentosa, elevated intraocular pressure, photoreceptor degeneration, intraocular neovascularization, vitreoretinopathy, retinal degeneration, retinal ischemia, retinal neovascularization, retinal pigment epithelium disease, and trachoma.

Example 4. In Vitro Release of Cyclosporine from Cyclosporine-Loaded Lacrisert Halves An ocular insert was prepared and drug-loaded as follows. Individual Lacrisert® rods were split length-wise in approximately half portions to provide the half rods or half-cylinders. The half rods, when viewed from an end, had a semi-circular shape. The half rods were then placed individually in a trough and soaked in a 100% tritiated ($^3$H) Cyclosporine (T-CsA) in ethanol (0.0125 mg per half Lacrisert or half rod, 2 µL). The amount of the Cyclosporine used per half rod was equivalent to half of that in a commercial Cyclosporine eye drop. Using a trough plexiglass mold, two Lacrisert halves were aligned per well/trough. The trough was sized to approximate the size of the half rod such that the shape of the half rod was maintained substantially by the trough during the soaking. The hot Cyclosporine (0.0125 mg, 2 µL) in ethanol were pipetted onto each Lacrisert half. The Lacriserts were allowed to dry in the mold for 1 hr at room temperature. The mold was then placed in a vacuum oven at 20 psi for 20-24 hrs at 37° C. The dried Lacrisert halves were removed from the mold halves with tweezers. Sixteen T-CsA-loaded Lacrisert were measured to give a baseline load. For comparison, tritiated ($^3$H) Cyclosporine drops in ethanol and mineral oil (0.05%, 0.0125 mg per drop) were prepared by mixing of 2 µL tritiated ($^3$H) Cyclosporine (100%) in ethanol and 23 µL mineral oil. The commercial Cyclosporine drop contains 0.025 mg of Cyclosporine in a glycerine/oil base.

The in vitro release was tested as follows. One set (2 Lacrisert halves=1, n=8) of loaded Lacrisert Halves® were placed into microcentrifuge tubes with balanced salt solution (BSS, 750 µL) and agitated in a water bath (Labline Orbit Shaker Bath 3540) at 34° C. and 100 rpm. At each hour for 8 hours, the tubes were removed from the water bath. The BSS was removed from each tube for counting. The BSS (750 µL) was replenished in the original tubes and those tubes returned to the water bath. The six 100 µL aliquots of the removed BSS were individually placed in labeled liquid scintillation vials with 5 mL of Universol. The activity of each vial was then read for 2 mins in a scintillation counter (Perkin Elmer Liquid Scintillation Analyzer Tri Carb 2900

TR) and recorded. The mean activity of the aliquots from each time period were then multiplied to equal that for 750 µL. At the end of the 8 hr period, each of the remaining Lacriserts was also read. These tests were performed twice.

Figure 8:
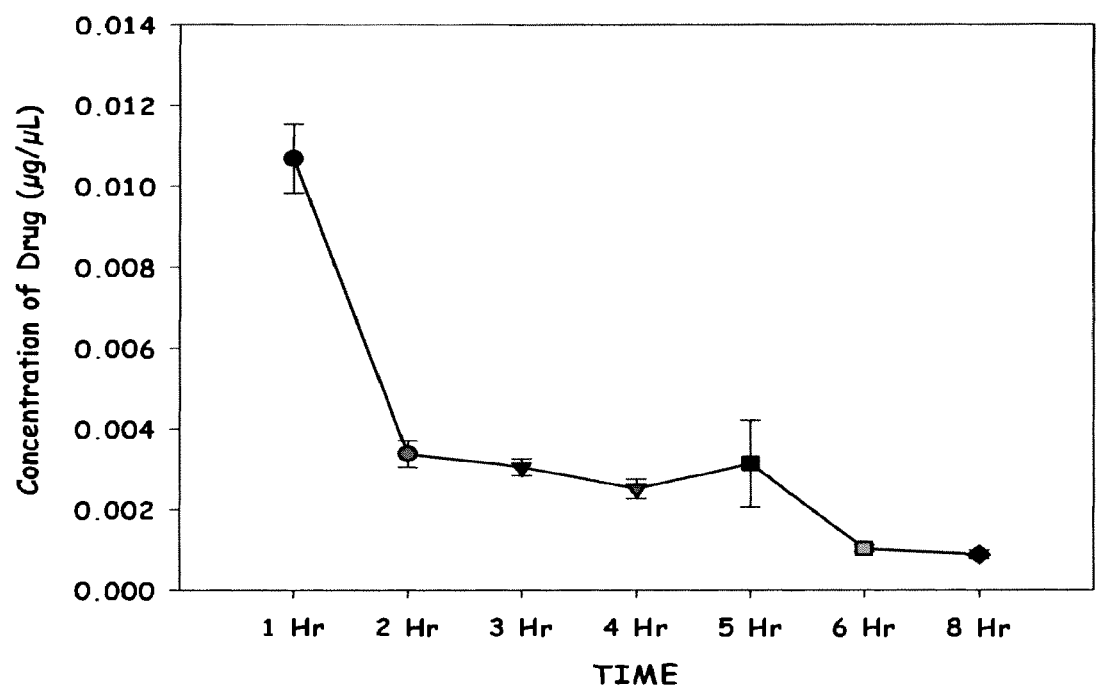
FIG. 8 graphically illustrates the mean Cyclosporine release from Lacrisert halves, a shaped delivery device of the present invention, which are loaded with Cyclosporine for 2 tests over 8 hour periods, as described in greater detail in the examples.

FIG. 8 graphically illustrates the mean Cyclosporine release from a pair of Lacrisert halves over the 8 hour period for the two tests. A mean total of 0.0247±0.00117 mg of Cyclosporine was eluted from two Lacrisert halves in vitro. The two Lacrisert halves contained an average of 0.0247 mg of drug, demonstrating that a hydrophobic drug can be effectively loaded to Lacrisert halves using, e.g., a drug solution in ethanol. In vitro, the Lacrisert released all of the Cyclosporine after 8 hours with at least about 50% of the drug delivered within the first hour. Other polar organic solvents (e.g., ethyl acetate, methanol, acetone and the like) may also be used, as well as non-polar organic solvents (e.g., ether, chloroform, methylene chloride), depending on the solubility characteristics of the API. Mixture of organic and aqueous (including buffered solutions) solvents may also be suitable.

Example 5. In Vivo Administration of Cyclosporine to Cornea and Scleral Rim from Cyclosporine-Loaded Lacrisert Halves Thirty-six rabbit eyes were prepared by removal of the nictitating membranes prior to administration. The eyes were divided into the following groups.

|  | $^3$H-CsA-Drops | $^3$H-CsA-Lacrisert Halves | Lacrisert (control - no drug) |
| --- | --- | --- | --- |
| Eyes | 16 | 16 | 4 |

Two drops of drug or two Lacrisert halves were placed pre-corneally in one eye of each rabbit. The loaded Lacrisert halves were prepared as described in Example 4. Twelve hours later, the rabbits were sacrificed. At the time of sacrifice, tears and aqueous humor were collected, volumes noted, and placed in individually labeled tubes. The cornea, corneoscleral rim (the scleral rim), and iris were then harvested from the eye. The tissues were harvested by cutting into the sclera approximately 3 mms outside of the cornea-limbal rim. The sclera was then cut circumferentially around the cornea-limbal rim to include 3 mm of sclera. The interior of the removed section included the iris. Once the cornea/sclera cap was removed from the eye, the interior iris was pulled away and placed in a labeled tube. The central cornea was then trephined with a 10 mm trephine. The remaining corneal-sclera, which included approximately 3 mm of cornea and 3 mm of sclera, was collected. All of the tissue tubes were weighed prior to scintillation counting. Universol fluid (5 mL) was placed in each tube, held at room temperature for 24 hours for maximum interaction between the $^3$H and the Universol, and the counts per minute read for 2 mins per sample using a scintillation counter.

Figure 9:
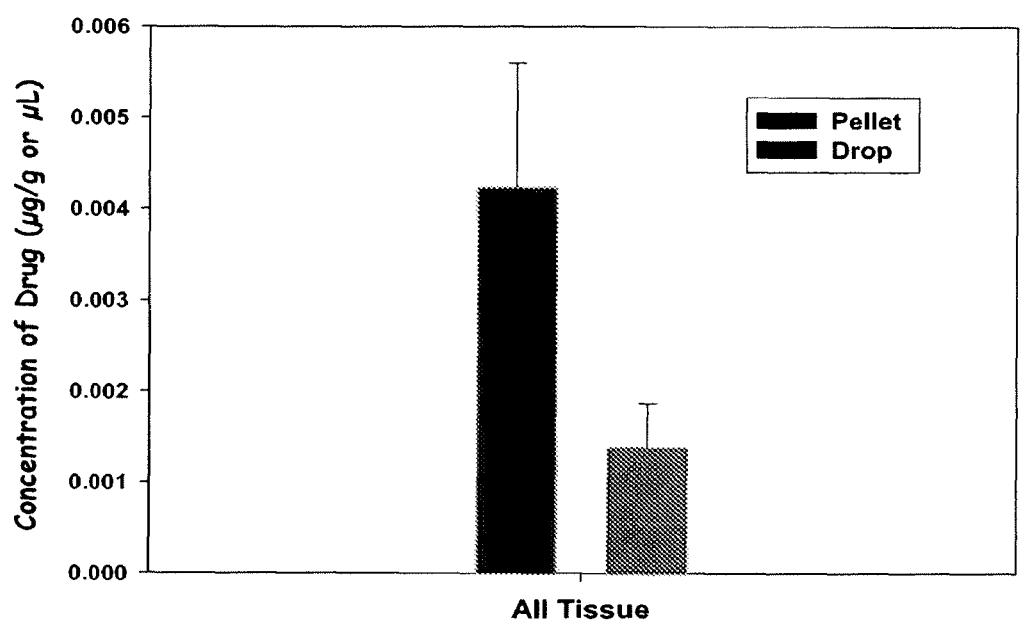
FIGS. 9 (all tissues) and 10 (various tissues) graphically illustrate the amount of Cyclosporine retained in ocular tissues, as delivered by Cyclosporine-loaded Lacrisert halves, at the end of a 12 hour experimental period, as described in greater detail in the examples.
Figure 10:
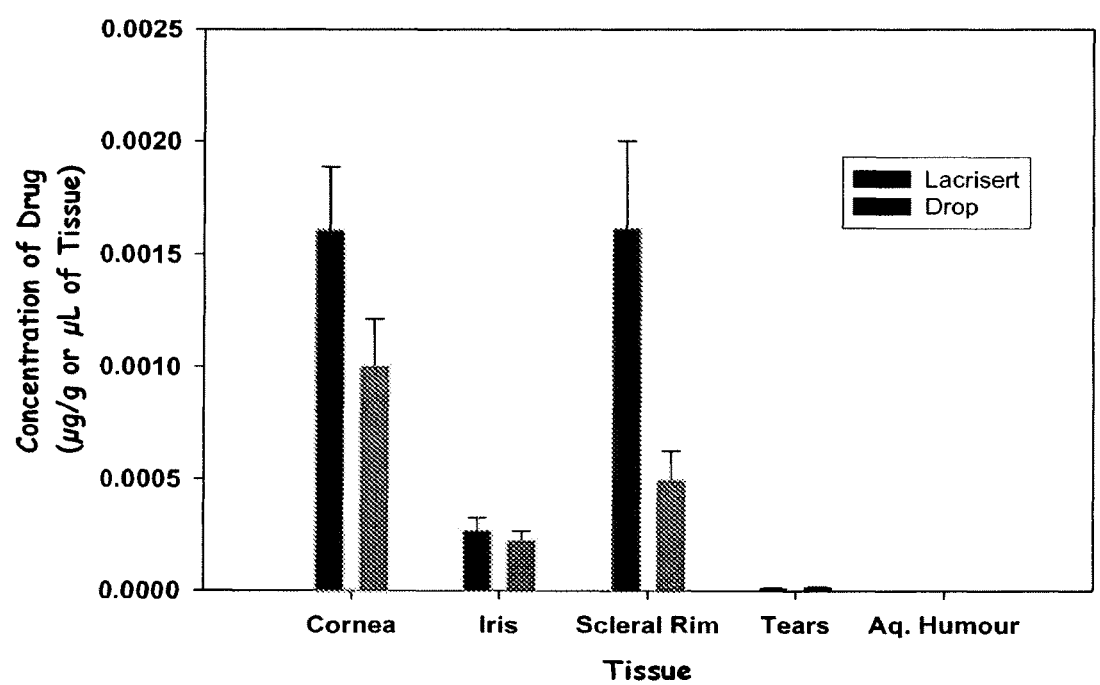

FIGS. 9 and 10 graphically illustrate the amount of Cyclosporine retained in, and at least administered to, various ocular tissues at the end of the 12 hour experimental period. The total mean concentration of drug still in the ocular tissue was $3.49 \times 10^{-3} \pm 6.27 \times 10^{-4}$ µg per g (for solid tissues, for example, cornea, sclera, iris and the like) or per µL (for fluid or liquid samples, for example, tears, aqueous humor and the like) for Lacrisert halves delivery versus $1.73 \times 10^{-3} \pm 1.37 \times 10^{-4}$ µg/g or µg/µL for delivery by eye drops. In vivo, Lacrisert halves delivered significantly more drug to the cornea and sclera than drops (p=0.005). Twelve hours after administration, there was 52% more Cyclosporine in the eyes when treated with the Lacrisert halves delivery system compared to eyes treated with eye drops.

Example 6. Drug Delivery by Latanoprost-Loaded Lacrisert Halves

This example demonstrates how Latanopost-loaded Lacrisert halves were made and their drug release profiles were tested in vitro and in vivo. The half rods or Lacrisert halves were prepared and loaded with the API in the following manner. Each Lacrisert was cut in half length-wise. The two halves were individually loaded with 0.725 mg of a 22% hot/78% cold Latanoprost mixture. So together their drug load equaled one drop of commercial Latanoprost (1.5 mg/drop), composed of 22% hot, tritiated ($^3$H) Latanoprost in ethanol (0.335 mg) and 78% cold, non-radioactive Latanoprost (1.165 mg, 1 Ci @ 500 µCi/mL, activity=10 Ci/mmol).

A mixture of hot (15.5 µL, 0.335 mg Latanoprost) and cold (19.4 µL, 1.165 mg Latanoprost) Latanoprost solutions were pipetted into plastic Eppendorf tube. Using razor blades, Lacriserts were cut and aligned lengthwise (2 per mold well). The molds, Lacriserts and the drug mixture were warmed in an oven (no vacuum) at 50° C. for approximately 30 minutes, and removed from the oven. The mixed drugs (8.725 µL) were pipetted over each Lacrisert half, and allowed to dry at 50° C. (no vacuum) for 30 min to an hour or until the liquid was absorbed into the Lacrisert half. The drug soaking and drying was repeated once so that each Lacrisert half received 17.45 µL of the mixed drug solution. The Lacrisert halves were kept overnight in vacuum at 20 psi and at 50° C., so that they were dry and firm. The Lacrisert halves were removed from the mold with tweezers. Sixteen T-Latanoprost-loaded Lacrisert halves were measured to give a baseline load. For comparison, commercial Latanoprost drops were augmented with 22% tritiated ($^3$H) Latanoprost in ethanol (0.335 mg per drop) were used so that one drop equaled 34.9 µL containing a total of 1.5 mg of Latanoprost.

A. In Vitro Release of Latanoprost

Figure 11:
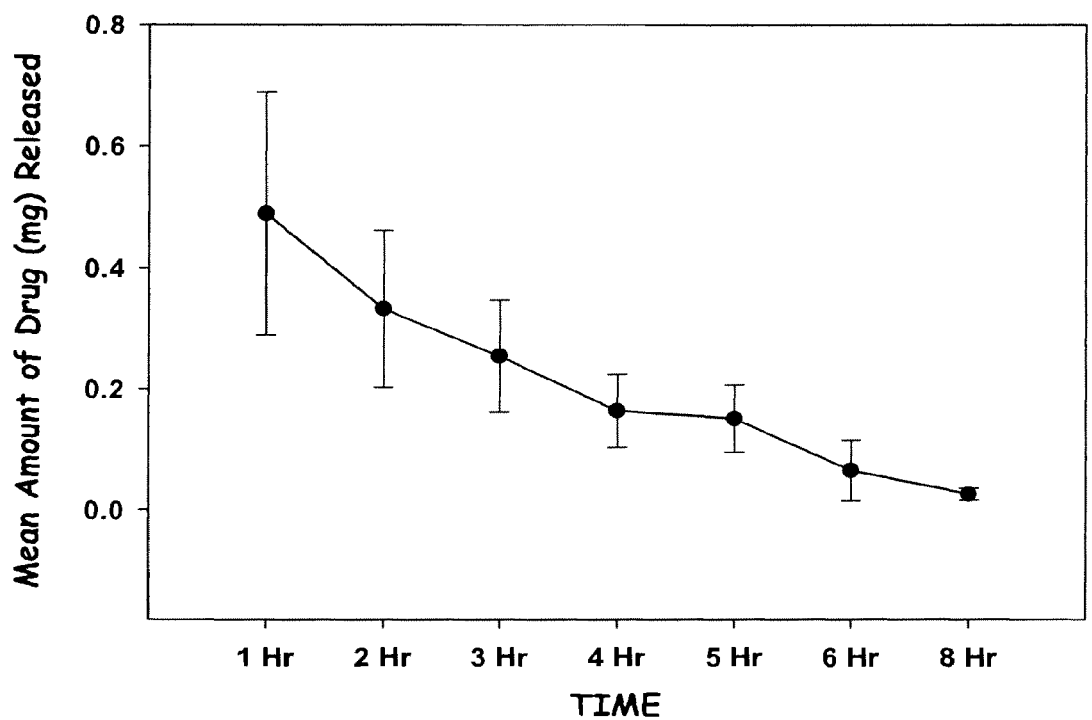
FIG. 11 graphically illustrates the mean Latanoprost release profile from Latanosport-loaded Lacrisert halves over an 8 hour period for 2 tests, as described in greater detail in the examples.

One set (2 Lacrisert halves=1, n=16) of loaded Lacriserts were placed into microcentrifuge tubes with balanced salt solution (750 µL) and agitated in a water bath (Labline Orbit Shaker Bath 3540) at 34° C. and 100 rpm. At each hour for 8 hours, the tubes were removed from the water bath. The BSS (750 µL) was removed from each tube for counting. The BSS were replenished (750 µL) in the original tubes and those tubes returned to the water bath. The six 100 µL aliquots of the removed BSS were individually placed in labeled liquid scintillation vials with 5 mL of Universol. The activity of each vial was then read for 2 mins in a scintillation counter (Perkin Elmer Liquid Scintillation Analyzer Tri Carb 2900 TR) and recorded. At the end of the 8 hour period, each of the remaining Lacriserts was also read. These tests were performed 2 times. The results are depicted in FIG. 11. A mean total of 1.486±0.085 mg of Latanoprost was eluted over 8 hours from each Lacrisert in vitro. These tests demonstrated how Latanoprost-loaded Lacrisert halves were made and their drug release profile tested. Each whole Lacrisert (i.e., 2 Lacrisert halves) contained an average of 1.486 mg of drug. In vitro, the Lacrisert halves released all of the Latanoprost after 8 hours with approximately a third of the drug delivered within the first hour.

B. In Vivo Testing

Rabbits (18) had their nictitating membranes removed 1 week prior to experimentation. Eyes (36) were divided into the following groups

| | $^3$H-Latanoprost-Drops | $^3$H-Latanoprost-Lacrisert Halves | Lacrisert |
|---|---|---|---|
| Eyes | 16 | 16 | 4 |

Figure 12:
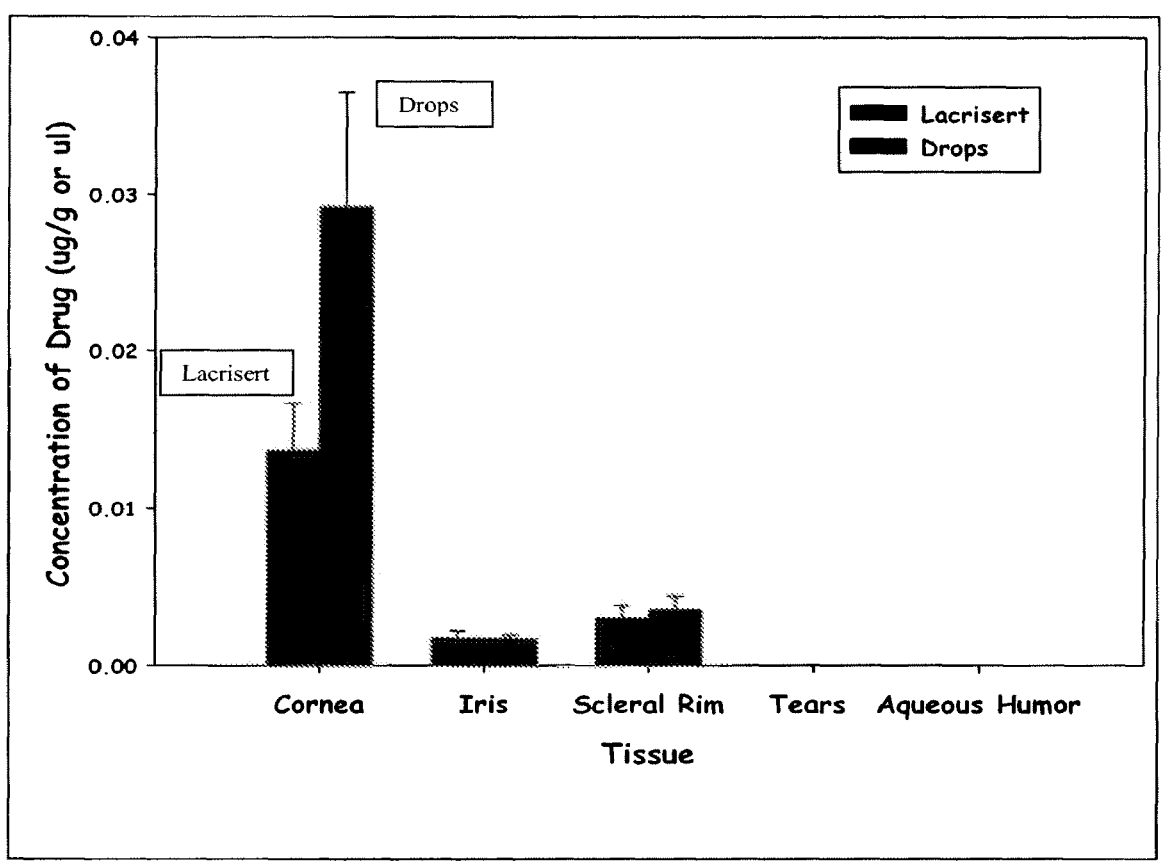
FIG. 12 graphically illustrates the amount of Latanoprost retained in various ocular tissues, as delivered by Latanosport-loaded Lacrisert halves, at the end of the 12 hour experimental period, as described in greater detail in the examples.
Figure 13:
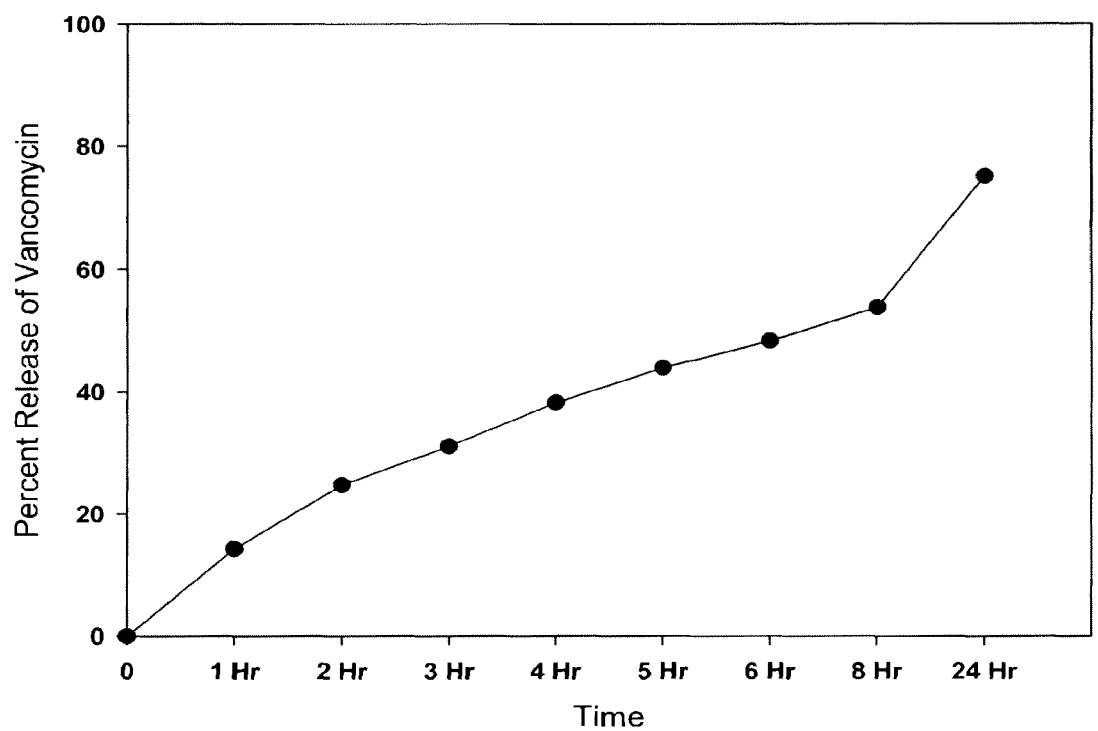
FIG. 13 graphically illustrates the drug release profile of Vancomycin-loaded Lacrisert halves, as described in greater detail in the examples.
Figure 14:
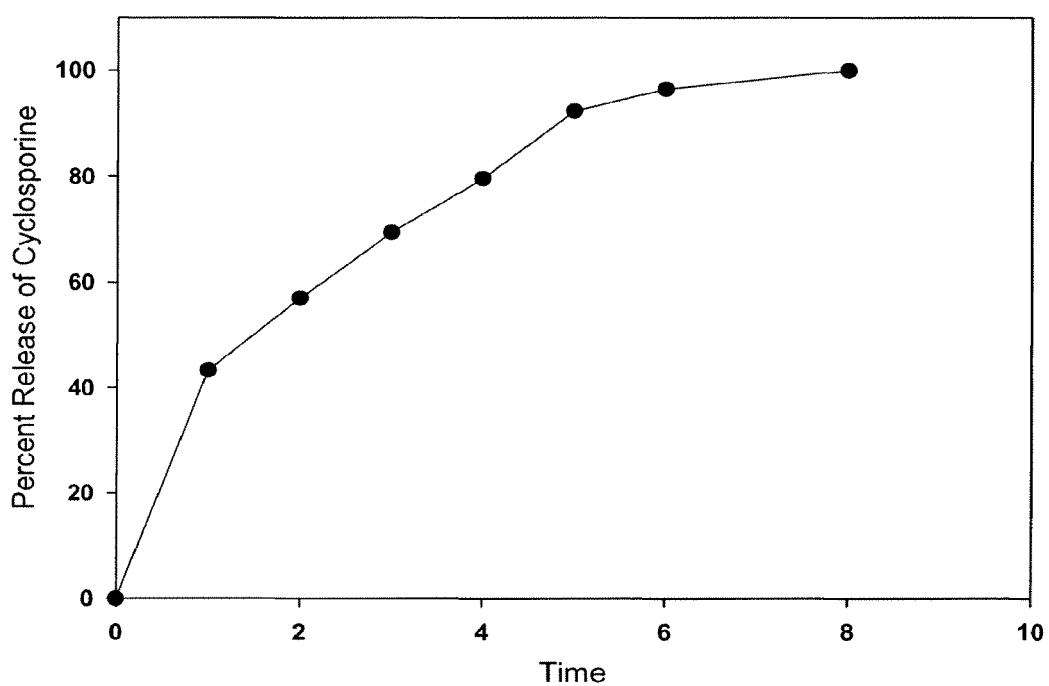
FIG. 14 graphically illustrates the drug release profile of Cyclosporine-loaded Lacrisert halves, as described in greater detail in the examples.

One drop of drug or two Lacrisert halves (loaded or unloaded) were placed pre-corneally in one eye of each rabbit. Twelve hours later, the rabbits were sacrificed. At the time of sacrifice, tears and aqueous humor were collected, volumes noted, and placed in individually labeled tubes. Then the cornea, corneoscleral rim, and iris were harvested from the eye. Tissue harvest was performed by cutting into the sclera approximately 3 mms outside of the cornea-limbal rim. The sclera was then cut circumferentially around the cornea-limbal rim to include 3 mm of sclera. The interior of the removed section included the iris. Once the cornea/sclera cap was removed from the eye, the interior iris was pulled away and placed in a labeled tube. The central cornea was then trephined out with a 10 mm trephine and placed in a separate labeled tube. The remaining corneal-scleral which included approximately 3 mm cornea and 3 mm sclera was placed in a separate labeled tube. All of the tissue tubes were weighed prior to scintillation counting. Universol fluid (5 mL) was placed in each tube, held at room temperature for 24 hours to maximize the interaction of $^3$H with the Universol, and the counts per minute read for 2 mins per sample using a scintillation counter. The results are depicted in FIG. 12. The total mean concentration of drug still in the ocular tissue was $34.44 \times 10^{-3} \pm 8.44 \times 10^{-3}$ mg/g (for tissues) or µL (for tears and such liquids) for drop delivery versus $18.42 \times 10^{-3} \pm 4.25 \times 10^{-3}$ mg/g or µl for the Lacrisert halves. In vivo, the Lacrisert halves delivered the drug into various ocular tissue. Under the test conditions, the drop delivered more drug to the cornea than did the Lacrisert halves.

Example 7. Drug Delivery by Betaxolol-Loaded Lacrisert Halves

This example demonstrates how Betaxoxlol-loaded Lacrisert halves were made and their drug release profiles were tested in vitro and in vivo. The half rods or Lacrisert halves were prepared and loaded with the API in the following manner. Each Lacrisert was cut length-wise in half. Each of the halves were loaded with 31.51 µg of 0.18% hot/99.82% cold Betaxolol so that together their drug load approximately equaled the drug load in one 25 µL drop of commercial Betaxolol (63.025 µg Betaxolol, composed of 0.18% tritiated ($^3$H) Betaxolol (0.525 µg) and 99.82% cold betaxolol (62.5 µg)). The concentration of commercial Betaxolol is 2.5 mg/mL. Patients are instructed to instill 1 drop (25 µL/drop) twice a day.

The hot [$^3$H]-Betaxolol available in ethanol was dried with nitrogen gas within the vial. Commercial Betaxolol (1 mL) was then added to the [$^3$H]-Betaxolol vial, the vial capped, and vortexed for 15 sec. Using a trough plexiglass mold, 2 lacrisert halves were aligned per trough (or well). The Betaxolol [$^3$H] mixture (6.25 µL, 15.75 µg) was pipetted onto each Lacrisert half. The Lacrisert halves were allowed to dry in the mold for 1 hr at room temperature. The Lacrisert halves appeared gel-like. An additional 6.25 µL of the Betaxolol [$^3$H] mixture was added to each half and the half allowed to air dry in the mold for 1 hr. A total of 12.5 µL (31.51 µg) of [3H]-Betaxolol was added to the Lacrisert half. The mold was then placed in a vacuum oven at 20 psi and 37° C. for 20-24 hr. The dried Lacrisert halves were removed from the mold with tweezers. Six whole [$^3$H]-Betaxolol-loaded Lacriserts (2 loaded halves=whole) were individually placed in scintillation vials with Universol (5 mL) and counted to give a baseline load.

A. In Vitro Release of Betaxolol

Figure 15:
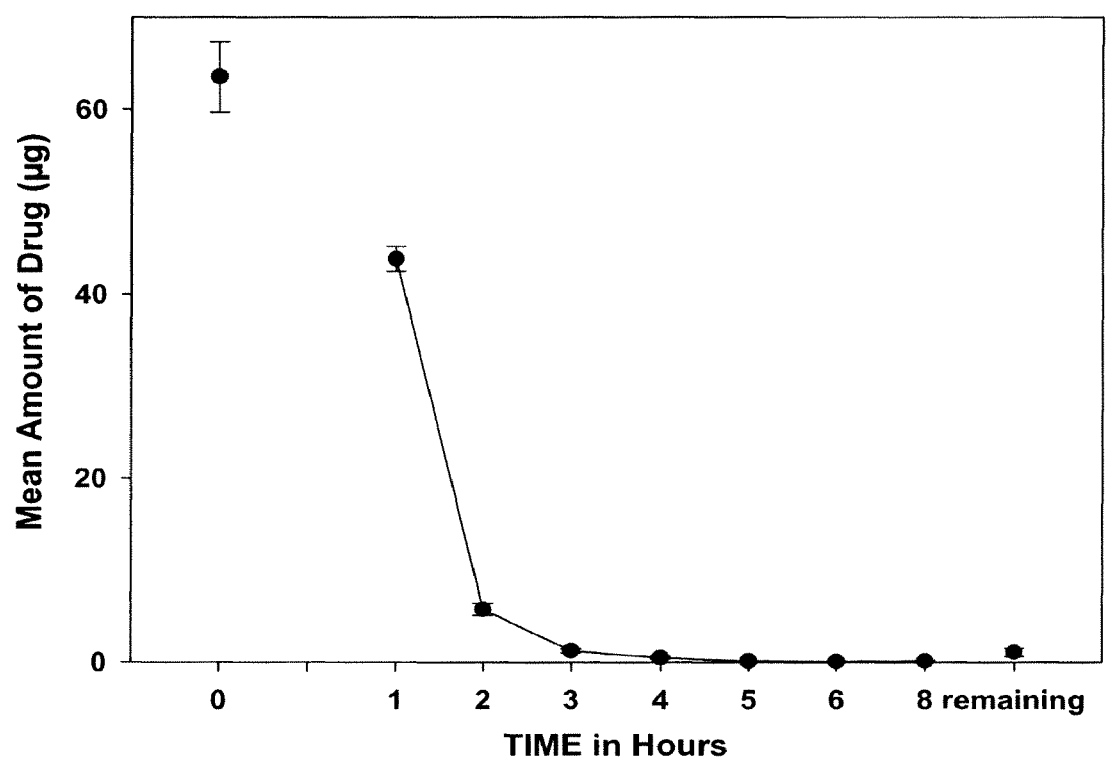
FIG. 15 graphically illustrates the average amount of Betaxolol released from Betaxolol-loaded Lacrisert halves, over an 8 hour period, as described in greater detail in the examples.
Figure 16:
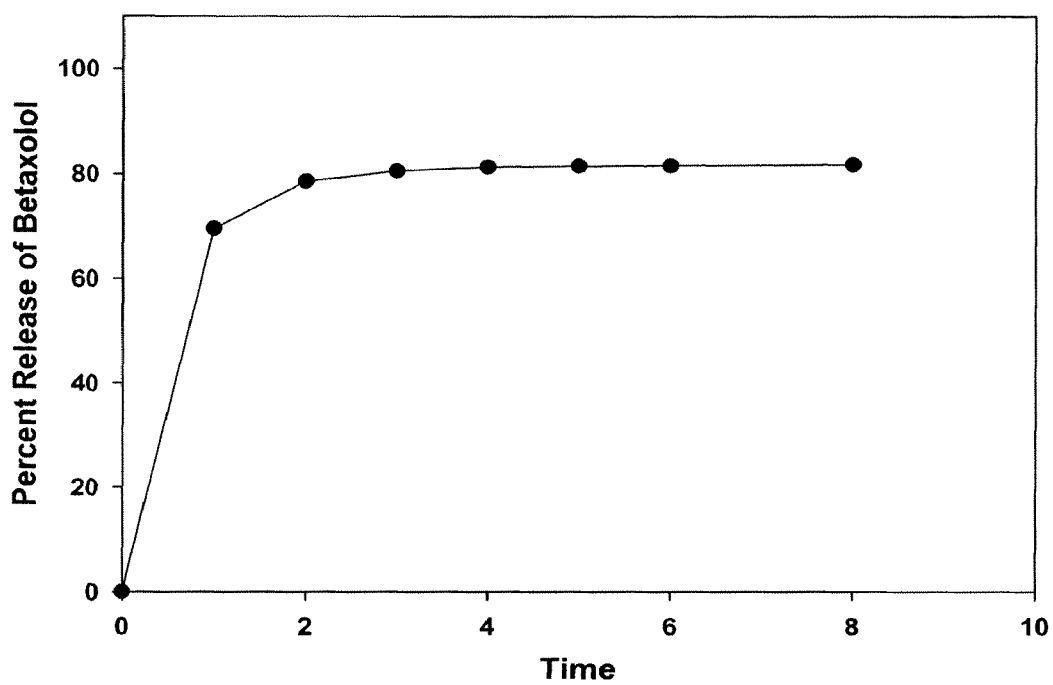
FIG. 16 graphically illustrates the percent release profile for the Betaxolol-loaded Lacrisert halves over an 8 hour period, as described in greater detail in the examples.

The release of Betaxolol from Betaxolol-loaded Lacrisert halves were performed as described in Example 6A above. The results are depicted in FIGS. 15 and 16. In vitro, the Lacrisert released all of the Betaxolol after 8 hours with more than 70% of the drug delivered within the first hour. FIG. 15 graphically illustrates the average amount released over the 8 hour period. A mean total of 51.53±11.495 µg of Betaxolol was eluted over 8 hours from each Lacrisert in vitro. In general, at the end of the experimental period, the Lacriserts were essentially just small clumps of HPC. Some of the API (1.098±0.431 µg) was associated with the remaining HPC. FIG. 16 graphically illustrates the percent release profile for the Betaxolol loaded Lacriserts over the 8 hour period.

B. In Vivo Testing

Figure 17:
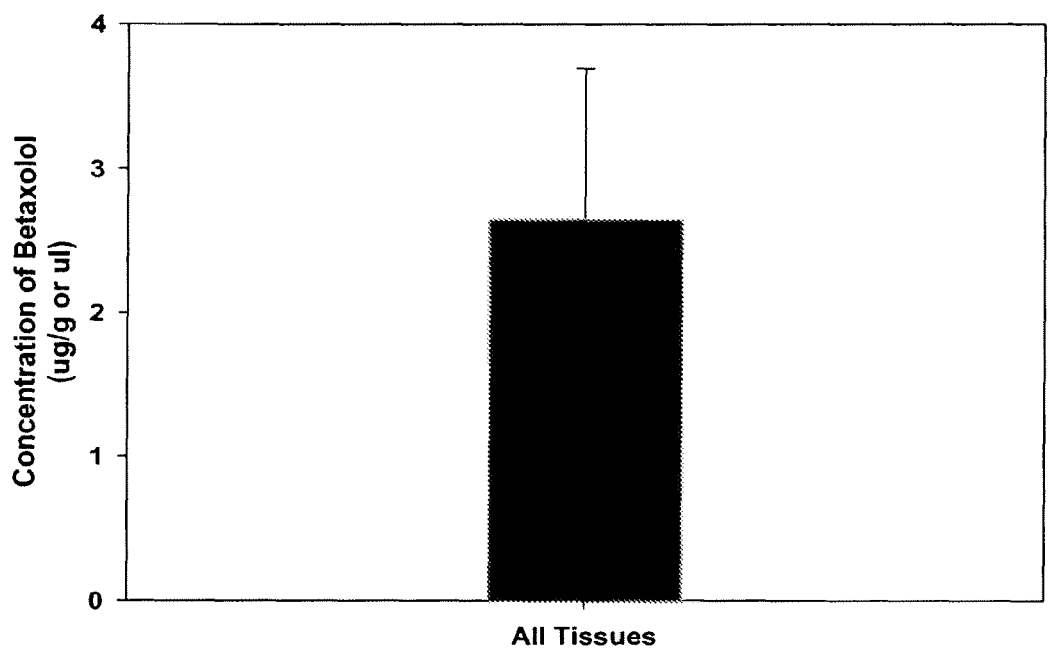
FIGS. 17 (all tissue) and 18 (various tissues) graphically illustrate Betaxolol concentration in the eye as delivered by Betaxolol-loaded Lacrisert halves 8 hours after administration, as described in greater detail in the examples.
Figure 18:
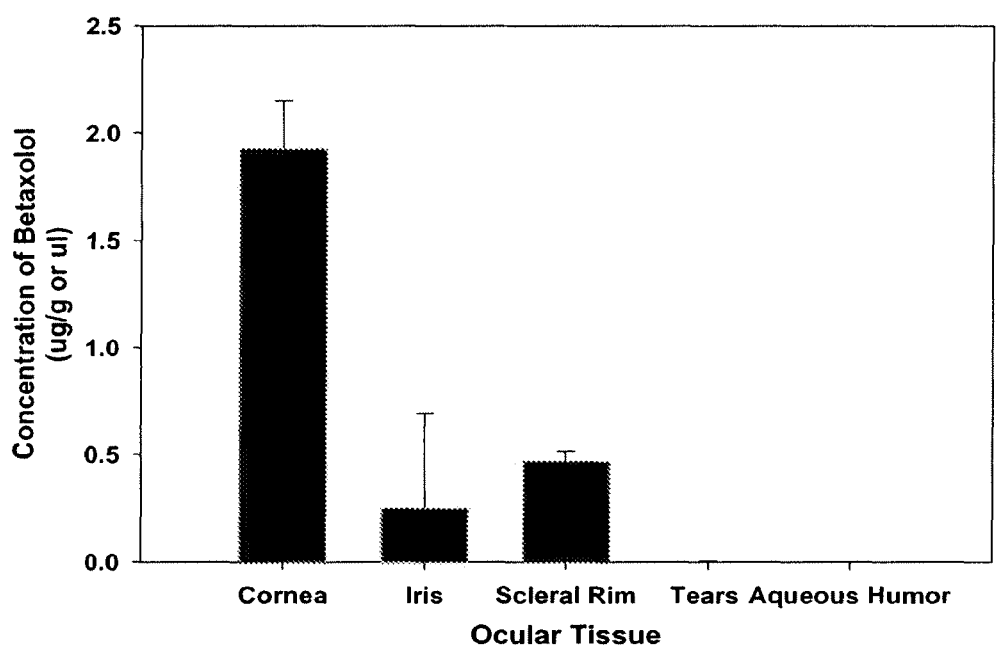

The administration of Betaxolol from Betaxolol-loaded Lacrisert halves was tested in vivo as described in Example 6B above. The results are depicted in FIGS. 17 and 18. After delivery by Lacrisert halves into the cul-de-sac of the eye, the total mean concentration of drug still in the ocular tissue was determined under the test conditions to be 2.64±1.05 µg/g or µL. The very low percentage (0.18%) of [3H]-Betaxolol molecules in the final drug mixture were problematic in some ways, which problems may however be easily eliminated by using, for example, a higher concentration of the hot API.

Example 8. Drug Delivery by Gentamicin-Loaded Lacrisert Halves

This example demonstrates how Gentamicin-loaded Lacrisert halves were made and their drug release profiles were tested in vitro and in vivo. The half rods or Lacrisert halves were prepared and loaded with the API in the following manner. Each Lacrisert was cut length-wise in half. Each half was loaded with 39.062 µg of 4% hot/96% cold Gentamicin sulfate so that together their drug load approximately equaled the drug load in one 25 µL drop of commercial Gentamicin (78.125 µg, composed of 4% tritiated ($^3$H) Gentamicin (3.125 µg) and 96% cold Gentamicin (75 µg)). The usual concentration of commercial Gentamicin is 3 mg/mL. Patients are instructed to add 1 or 2 drops (about 25 µL/drop) every four hours.

The hot [$^3$H]-Gentamicin in ethanol was dried with nitrogen gas within the original shipped vial. One mL of commercial Gentamicin was added to the [$^3$H]-Gentamicin vial, the vial capped, and vortexed for 15 sec. Using a trough plexiglass mold, 2 lacrisert halves were aligned per trough (or well). Then 6.25 µL of the Gentamicin [$^3$H] mixture (19.516 µg) were pipetted onto each Lacrisert half. The Lacrisert halves were allowed to dry in the mold for 1 hr at room temperature. The Lacrisert halves appeared gel-like. An additional 6.25 µL of the Gentamicin [$^3$H] mixture was added to each half and allowed to air dry in the mold for an hour. Therefore a total of 12.5 µL (39.062 µg) of [3H]-Gentamicin was added lacrisert half. The mold was then placed in a vacuum oven at 20 psi for 20-24 hrs at 37° C. The dried Lacrisert halves were remove from the mold halves with tweezers. Six [³H]-whole Gentamicin-loaded Lacriserts (2 halves=a whole) were placed in individual scintillation vials with 5 mL Universol and counted to give a baseline load.

A. In Vitro Release of Gentamicin

Figure 19:
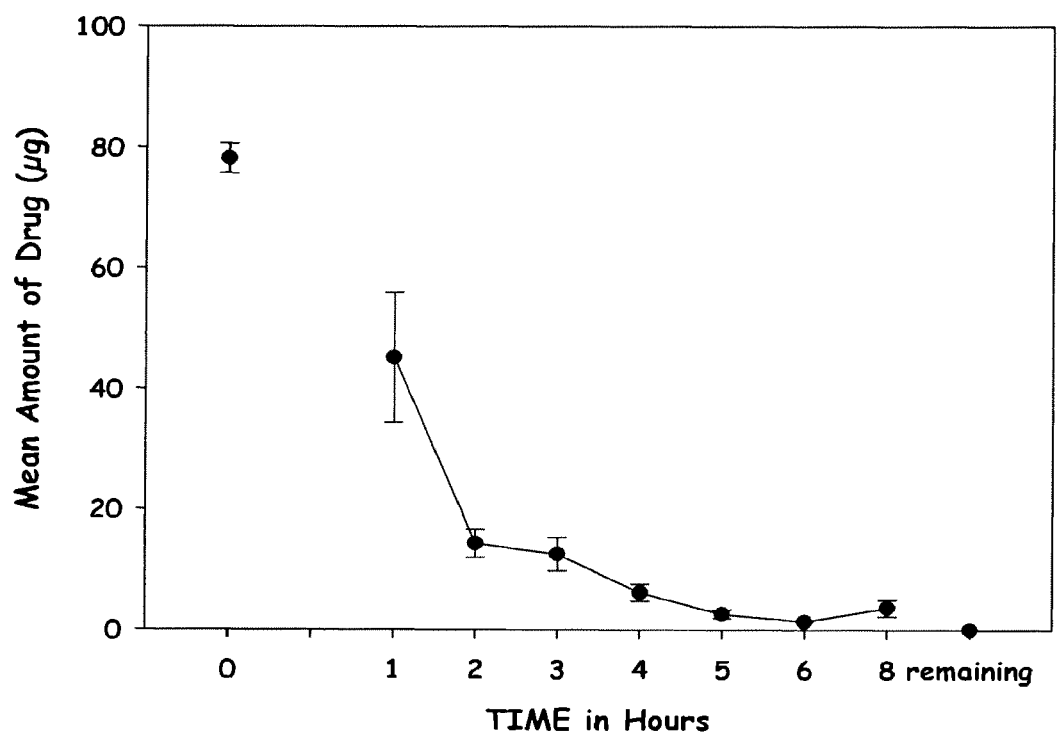
FIG. 19 graphically illustrates the average amount of Gentamicin released from Gentamicin-loaded Lacrisert halves, over an 8 hour period, as described in greater detail in the examples.
Figure 20:
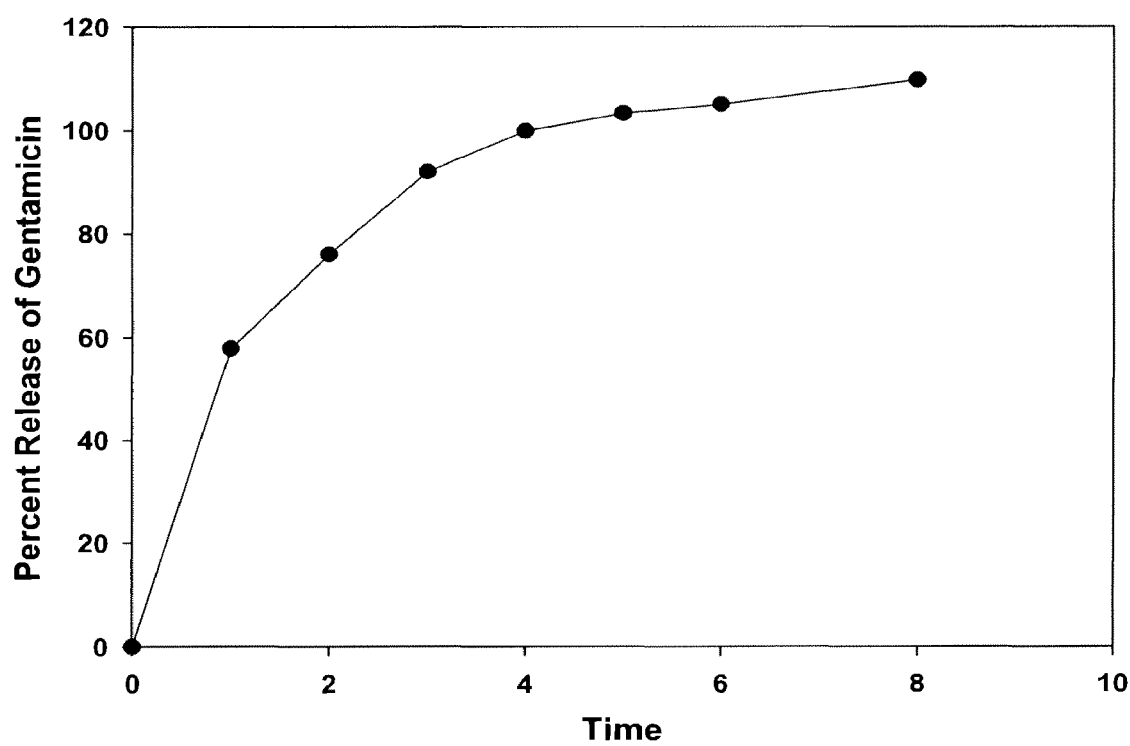
FIG. 20 graphically illustrates the percent release profile for the Gentamicin-loaded Lacrisert halves over an 8 hour period, as described in greater detail in the examples.

The release of Gentamicin from Gentamicin-loaded Lacrisert halves were performed as described in Example 6A above. The results are depicted in FIGS. 19 and 20. In vitro, the Lacrisert released all of the Gentamicin after 8 hours with more than 50% of the drug delivered within the first hour. In vivo, there was a significant amount of drug delivered to the eye by Lacriserts. FIG. 19 graphically illustrates the average amount of Gentamicin released over the 8 hour period. A mean total of 85.690±7.565 µg of Gentamicin was determined to have been released over 8 hours from each whole Lacrisert in vitro. In general, at the end of the experimental period the Lacriserts were essentially just small clumps of HPC. No drug was associated with the remaining HPC. FIG. 20 graphically illustrates the percent release profile for the Gentamicin-loaded lacriserts over the 8 hour period.

B. In Vivo Testing

Figure 21:
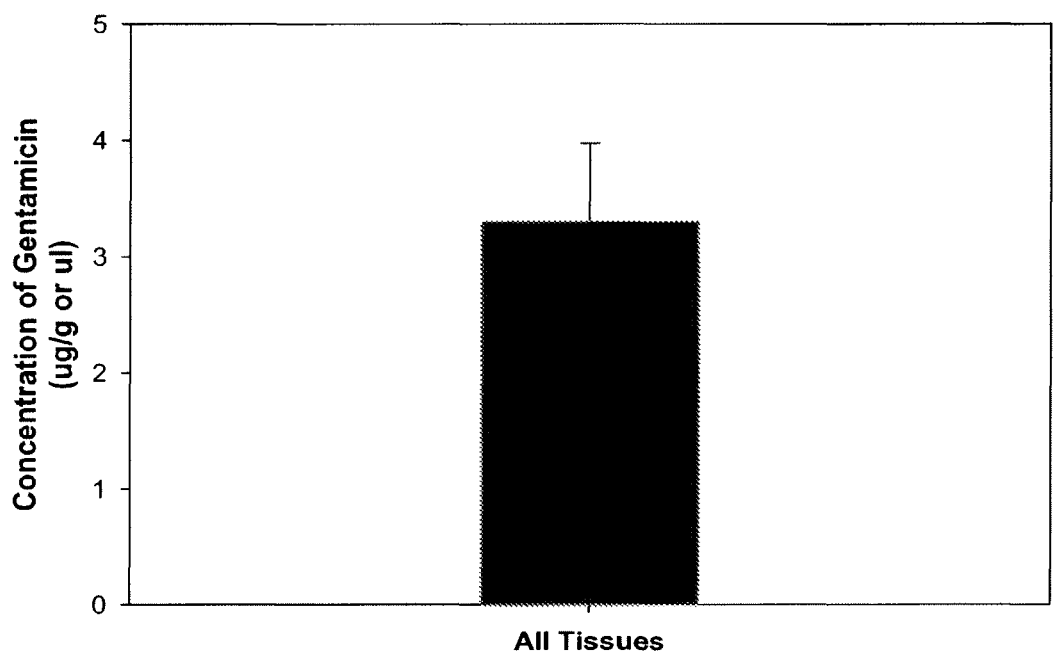
FIGS. 21 (all tissues) and 22 (various tissues) graphically illustrate Gentamicin concentration in the eye as delivered by Gentamicin-loaded Lacrisert halves 8 hours after administration, as described in greater detail in the examples.
Figure 22:
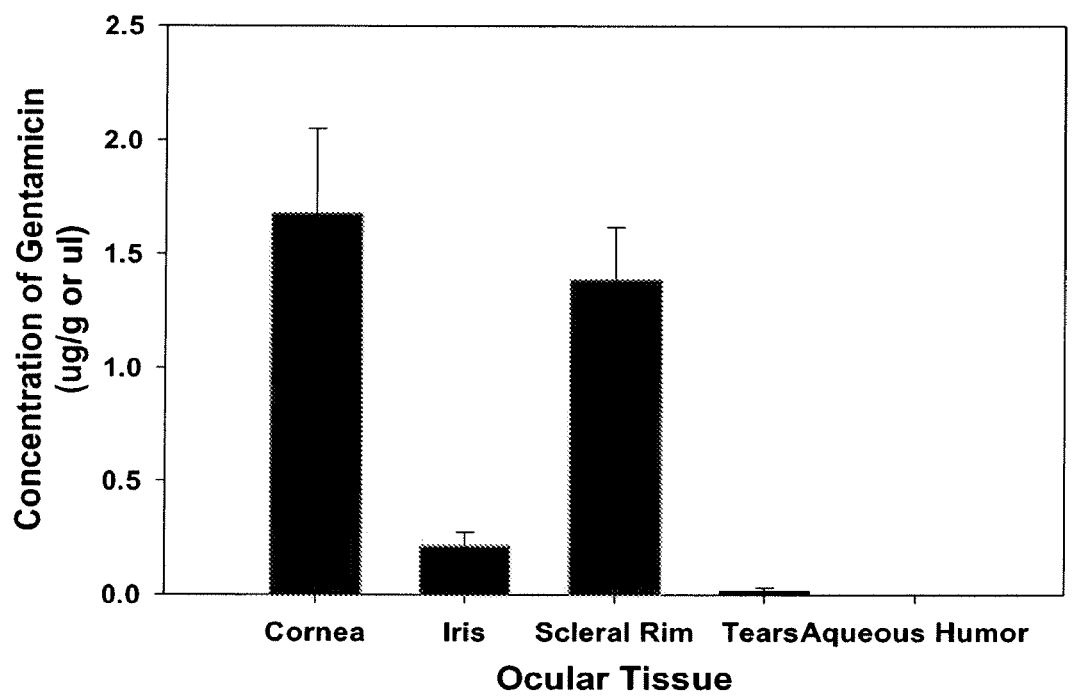

The administration of Gentamicin from Gentamycin-loaded Lacrisert halves was tested in vivo as described in Example 6B above. FIGS. 21 and 22 show the amount of Gentamicin retained in the ocular tissues at the end of the 8 hour test period. The total mean concentration of drug still in the ocular tissue was 3.30±0.69 µg/g or µL for Lacrisert delivery. In vitro, the Lacrisert released all of the Gentamicin after 8 hours with more than 50% of the drug delivered within the first hour. In vivo, there was a significant amount of drug delivered to the eye by the Lacrisert halves.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method of forming an ocular delivery device comprising:
    placing a solid, shaped cellulose polymer in a vessel adapted to restrict the swelling of the polymer in at least one direction;
    exposing the solid, shaped cellulose polymer, while in said vessel, to a solution comprising an active pharmaceutical ingredient and a solvent capable of solubilizing said active pharmaceutical ingredient, wherein the polymer absorbs at least a portion of the solution, including the active pharmaceutical ingredient and solvent;
    allowing the absorbed solvent to evaporate from the polymer or drying the polymer; and
    freeing the polymer from the vessel.

2. The method of claim 1, wherein the at least one direction is a radial direction.

3. The method of claim 1, wherein the shape and dimension of an interior surface of the vessel substantially matches the shape and dimension of an exterior surface of the polymer.

4. The method of claim 1, wherein the interior surface of the vessel is coated with a surface-release agent.

5. The method of claim 1, wherein the ocular delivery device is capable of releasing the active pharmaceutical ingredient upon exposure of the ocular delivery device to a medium.

6. The method of claim 5, wherein the release of the active pharmaceutical ingredient from the ocular delivery device is substantially zero-order from about two to about six hours after exposing the ocular delivery device to the medium.

7. The method of claim 1, comprising drying the polymer under vacuum.

8. The method of claim 1, wherein the polymer is selected from hydroxymethyl cellulose, hydroxyethyl cellulose, hydroxypropyl cellulose, hydroxypropylmethyl cellulose, or a mixture of any two or more thereof.

9. The method of claim 1, wherein the active pharmaceutical ingredient is thermally unstable above about 80° C.

10. The method of claim 1, wherein the active pharmaceutical ingredient is selected from the group consisting of Acebutolol, Acyclovir, Betaxolol, Bimatoprost, Brimonidine Tartrate, Brinzolamide, Bromfenac Sodium, Cefazolin, Cephalexin, Cephadroxil, Ciprofloxacin, Ciprofloxacin HCl, Cyclosporine, Dexamethasone, Dorzolamide HCl, Epinastine HCl, Erythromycin, Gancicylovir, Gatifloxacin, Gentamicin Sulfate, Ketorolac Tromethamine, Labetalol, Latanoprost, Loteprednol Etabonate, Moxifloxacin HCl, Nepafenac, Ofloxacin, Olopatadine HCl, Penicillin, Pindolol, Prednisolone, Propanolol, Polymyxin B Sulfate/Trimethoprim Sulfate, Sulfacetamide Sodium, Timolol Maleate, Triflourodine, Tobramycin, Travoprost, Vancomycin, Azelastine HCl, Atropine sulfate, Betamethasone, Carbachol, Pheniramine, Cromolyn sodium, Cyclopentolate, Demecarium bromide, Dexamethasone 21-phosphate, Erythromycin Base, Fluorometholone, Gatifloxacin, Homatropine, Hydroxyamphetamine, Idoxuridine, Medrysone, Methylprednisolone, Naphazoline, Resolvins, Phospholipids, Phenylephrine, Phospholine iodide, Prednisolone Acetate, Prednisolone Sodium Sulfate, Sulfisoxazole, Tetrahydrazoline HCl, Timolol, Tobramycin Sulfate, Tropicamide, 6-hydroxy-2-sulfamoylbenzo[b]thiophene, 6-acetoxy-2-sulfamoylbenzo[b]thiophene, 5,6-dihydro-4H-4-hydroxythieno[2,3-b]thiopyran-2-sulfonamide-7,7-dioxide, and mixtures of any two or more thereof.

11. The method of claim 1, wherein the solid, shaped cellulose polymer is in the shape of
    a half-cylinder, and the vessel comprises a trough; and wherein the trough maintains the shape of the half-cylinder during the exposing.

12. The method of claim 11, wherein the half-cylinder has a proximal end, a distal end, a diameter of about 0.5 mm to about 4 mm and a length of about 0.5 mm to about 7 mm.

13. The method of claim 11, wherein the half-cylinder has a surface area to volume ratio greater than about 4 mm²:mm³.

14. The method of claim 11, wherein the half-cylinder has a surface area to volume ratio of about 5 mm²:mm³ to about 6 mm²:mm³.

15. The method of claim 1, wherein the active pharmaceutical ingredient is Vancomycin or a mixture of Vancomycin and Tobramycin.

16. The method of claim 1, wherein the active pharmaceutical ingredient is Cyclosporine.

17. The method of claim 1, wherein the polymer comprises more than 30 wt % hydroxypropyl cellulose.

18. The method of claim 1, wherein the polymer consists essentially of hydroxypropyl cellulose.

19. The method of claim 1, wherein the solvent comprises ethanol.

20. The method of claim 1, wherein the solid, shaped, cellulose polymer has a length from about 1 mm to 7 mm and a width from about 1 mm to 4 mm.

* * * * *